United States Patent [19]
Prince et al.

[11] Patent Number: 5,112,298
[45] Date of Patent: May 12, 1992

[54] APHERESIS METHOD AND DEVICE

[75] Inventors: Paul R. Prince, San Juan Capistrano; William Miller, Santa Ana; Grant S. Benjamin, Costa Mesa, all of Calif.

[73] Assignee: Baxter International Inc., Deerfield, Ill.

[21] Appl. No.: 542,846

[22] Filed: Jun. 25, 1990

[51] Int. Cl.$^5$ .............................................. A61M 1/00
[52] U.S. Cl. ........................................ 604/6; 604/4; 604/5; 210/645
[58] Field of Search ....................... 604/4–6, 604/28; 210/645, 646, 790

[56] References Cited

U.S. PATENT DOCUMENTS

| | | | |
|---|---|---|---|
| 4,151,844 | 5/1979 | Cullis et al. | 604/6 |
| 4,185,629 | 1/1980 | Cullis et al. | 604/6 |
| 4,828,543 | 5/1989 | Weiss et al. | 604/4 |
| 4,850,998 | 7/1989 | Schoendorfer | 604/28 |
| 4,851,126 | 7/1989 | Schoendorfer | 604/6 X |
| 4,911,703 | 3/1990 | Lysaght et al. | 604/6 |
| 4,923,439 | 5/1990 | Seidel et al. | 604/6 |
| 4,944,883 | 7/1990 | Schoendorfer et al. | 604/5 X |
| 4,995,268 | 2/1991 | Ash et al. | 604/4 X |

Primary Examiner—Robert A. Hafer
Assistant Examiner—Kerry Owens
Attorney, Agent, or Firm—Robert D. Buyan

[57] ABSTRACT

A simplified fluid separation method and device usable for various apheresis procedures, including plasmapheresis. At least one pump is utilized to draw a first fluid (e.g. whole blood) into a separation device. The separation device then operates to separate the fluid (e.g. whole blood) into first and second fluid fractions (e.g. a cell concentrate and blood plasma). The first and second fluid fractions are pumped from the separation device to separate first and second fluid fraction containers, both of which are positioned on a single weighing device, such as an electronic load cell. At least one of the fluid fractions is subsequently removed from its fluid fraction container and returned to the human subject or other fluid source. Weights recorded by the single weighing device are then utilized to calculate the actual weights of fluid and/or fluid fractions pumped by at least one pump during the procedure. Such actual weights of fluid and/or fluid fractions are then utilized to calculate new pump flow constants, thereby enabling the calibration of the pump(s) to be corrected, on the basis of such new pump flow constants, prior to subsequent utilization of the pump(s) for pumping the fluid and/or fluid fractions. The single weighing device may also be utilized to monitor the weight change or rate of weight change occurring as the fluid fractions are pumped into and/or out of the fluid fraction containers, thereby providing a means for monitoring and verifying the pressures and flow rates within the system.

14 Claims, 17 Drawing Sheets

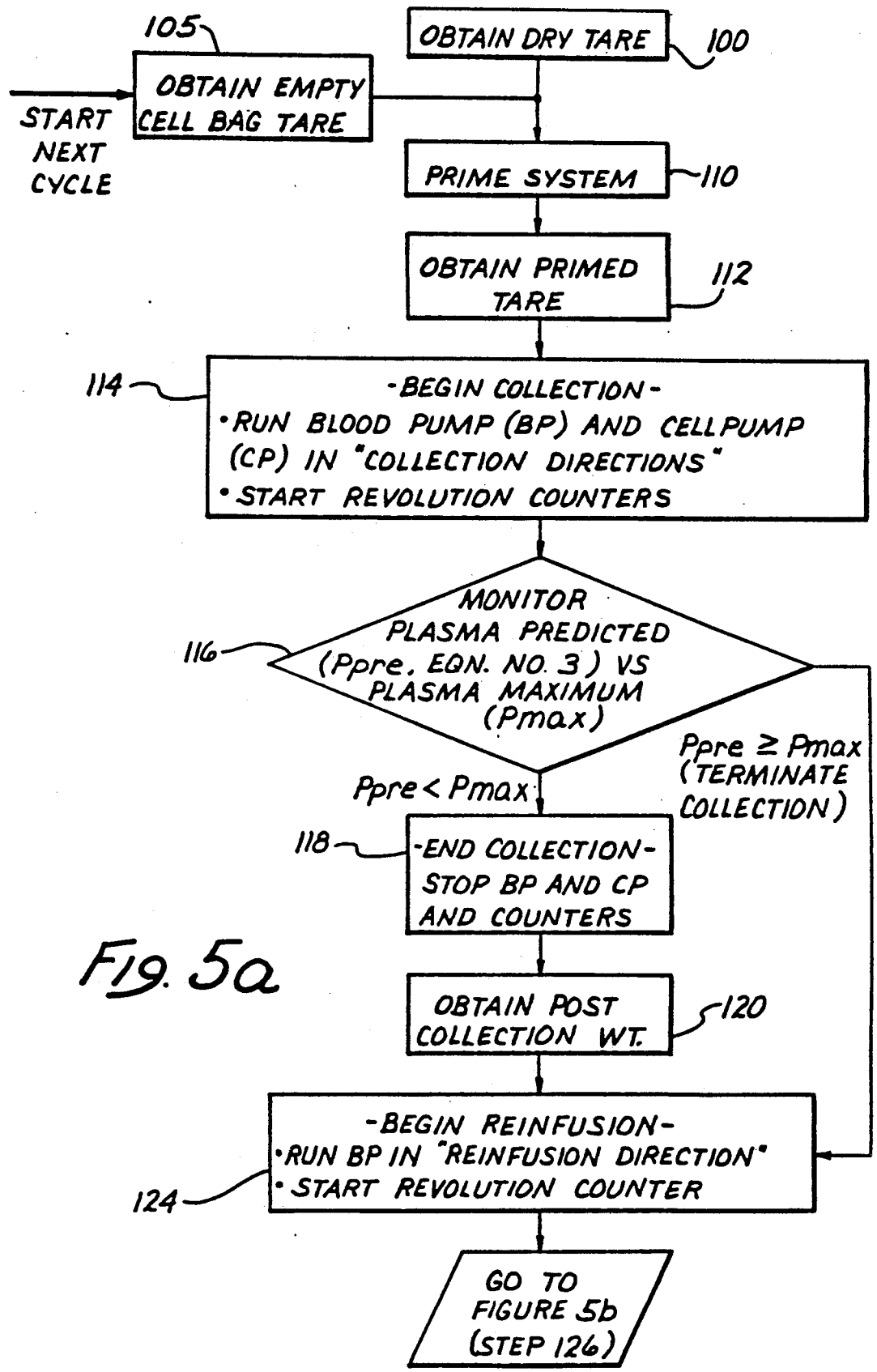

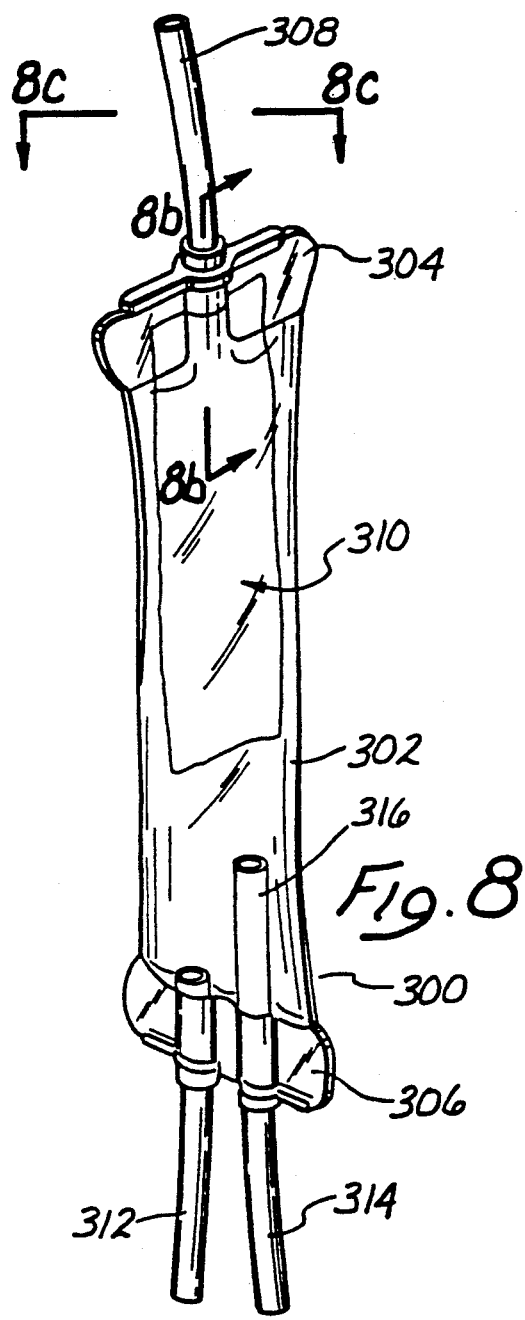
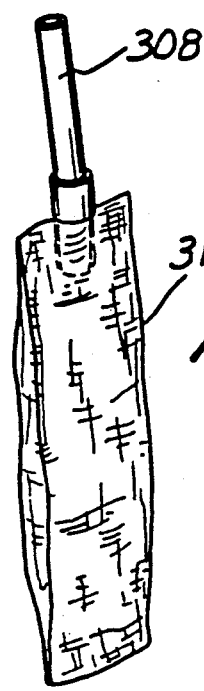
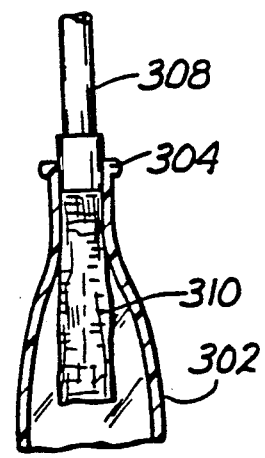
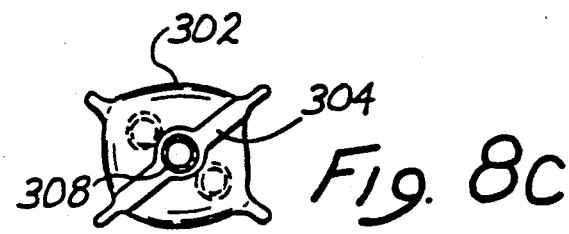

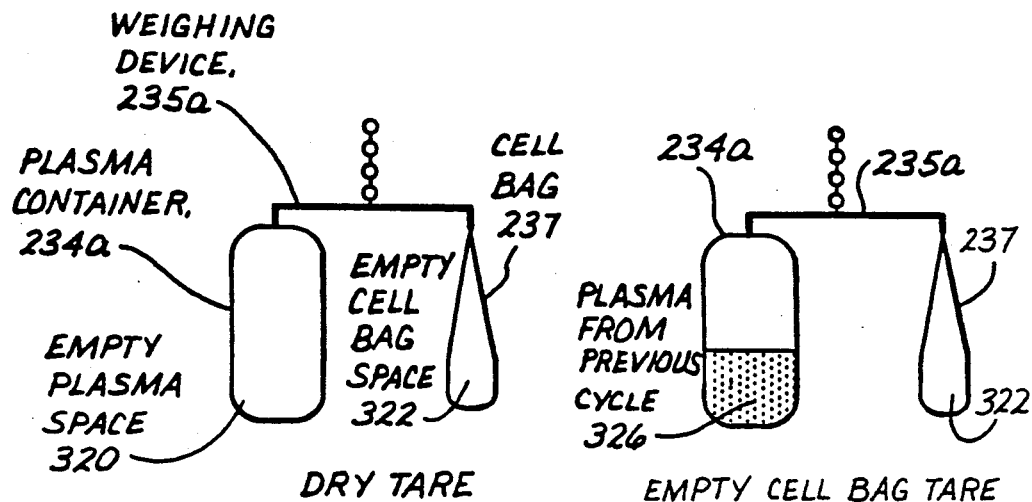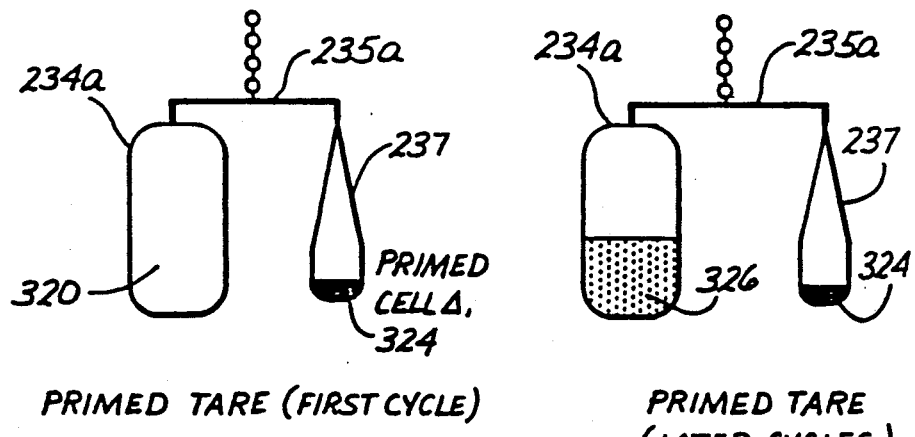

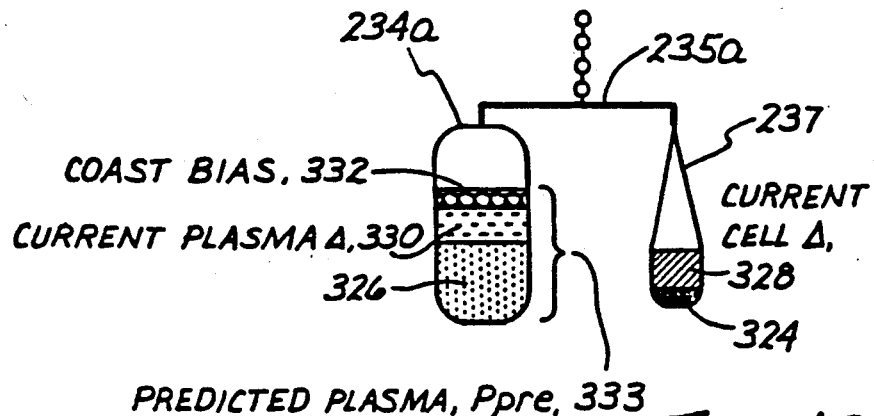
Fig. 10
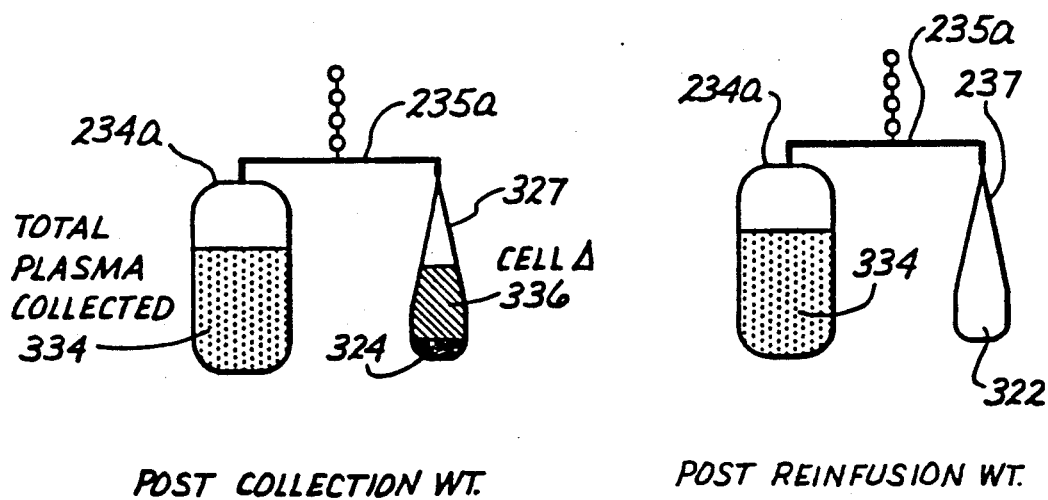
Fig. 11
Fig. 12

APHERESIS METHOD AND DEVICE

FIELD OF THE INVENTION

The present invention pertains generally to fluid processing equipment and more particularly to a method and device for effecting apheresis procedures.

BACKGROUND OF THE INVENTION

In current practice, there exist numerous situations in which it is desirable to efficiently separate fluids such as whole blood into two or more specific components (e.g. plasma, red blood cells, leukocytes, platelets, etc.). In commercial applications, it is often necessary to separate whole blood into two or more constituents in order that a specific blood constituent may be harvested and utilized for the preparation of medically useful blood derivatives or preparations (e.g. packed red blood cells, fresh frozen plasma, specific blood factors, etc.). Also, in therapeutic settings it is often desirable to separate whole blood into two or more constituents for purposes of treating or removing a specific constituent(s) of the blood in accordance with certain therapeutic protocols.

In almost all blood constituent separation procedures, whether commercial or therapeutic, quantities of whole blood are withdrawn from a human subject, the whole blood is then separated into two or more constituent fractions and at least one of the constituent fractions is subsequently transfused back into the human subject. The nonreinfused constituent fraction(s) may be retained for use in the preparation of various blood plasma products (e.g. fresh frozen plasma, albumin, or Factor VIII) or, in the therapeutic applications, may be discarded and replaced by plasma from a healthy donor or may be subjected to physical pharmacologic or radiologic treatment and subsequently returned to the human subject.

The general term "apheresis" used to describe three-step procedures wherein whole blood is a) withdrawn, b) separated into fractions and c) at least one of the fractions is retransfused into the human subject. Specific types of apheresis procedures include: "plasmapheresis" (for the collection of blood plasma), "leukapheresis" (for the collection of leukocytes), "thrombocytapheresis" (for the collection of platelets), therapeutic plasma exchange (wherein a portion of the subject's blood plasma is replaced with other fluids, such as plasma obtained from another human), and therapeutic plasma processing wherein a portion of the subject's plasma is separated, treated or processed and then returned to the subject.

Prior to the 1970's, when it was desired to separate whole blood into specific blood constituent(s), it was generally necessary to draw, on a unit by unit basis, quantities of whole blood from a human donor. Each unit of whole blood withdrawn was manually centrifuged to effect separation of the desired blood constituent or component and, thereafter, the remaining portions of the blood were manually reinfused into the donor. It was typically necessary to repeat such a procedure, on the same donor, several times (i.e. unit after unit) until the maximum allowable volume of plasma or other blood constituent had been collected.

More recently, automated apheresis machines been developed to minimize the degree of manual endeavor required when separating and collecting specific blood constituents. These automated apheresis machines typically comprise a central computer electrically connected to, and programmed to control, a system of tubes, vessels, filters and at least one blood separation device. The blood separation device is typically a rotating centrifugal filter or membrane which operates to separate the desired specific blood constituent(s) (e.g. plasma, cells, platelets, etc.). The typical automated apheresis machines of the prior art incorporate one or more "peristaltic pumps" or "tubing pumps" for moving blood, blood constituents and/or reagent solutions through the machine. Such "peristaltic pumps" or "tubing pumps" generally consist of a series of rotating rollers or cams over which a length of plastic tubing is stretched. Rotation of the cams or rollers then serves to dynamically compress regions of the tubing so as to move the desired fluids through the tubing at a desired rate. The use of such peristaltic pumps is particularly suitable in automated apheresis equipment because the mechanical working components of such pumps do not come in contact with the blood or other fluids being pumped, thereby preventing contamination of such fluids. Moreover, the use of peristaltic pumps permits intermittent disposal and replacement of the attendant tubing, as is commonly done to maintain sterile and hygienic conditions during each blood donation procedure. These peristaltic pumps are, however., given to a great deal of uncertainty or "drift" in calibration. Such uncertainty or "drift" in the pump calibration occurs because of variations in the size and material consistency of the pump tubing, variations in the rotational speed of the pump cam or rollers, stretching and/or wear of the pump tubing, etc. The resultant variations in the throughput of the peristaltic pumps complicates the operation of automated apheresis machines because such variations in pump throughout render it difficult to accurately control volume of blood or blood constituents collected in a particular procedure. Strict control of the volumes of blood or blood constituents withdrawn is required by governmental regulation intended to prevent inadvertent or purposeful over-withdrawal of blood or specific blood constituents from the human subject, as may result in injury to the human subject. Furthermore, variations in throughput of the pumps is problematic because many steps in automated apheresis procedures require precise knowledge of actual fluid flow rates. Also, certain system components, such as the separator device 20 require pressure and flow control in order to operate safely and efficiently.

In view of the above-stated shortcomings of the prior art automated apheresis machines, there exists a need for new apheresis machines and/or methods which minimize the expense and/or complexity of apheresis procedures, without any prohibitive diminution in the ability to monitor and maintain accurate control of the calibration and throughput of the blood and other fluids being extracted from the human subject and processed by the apheresis machine.

SUMMARY OF THE INVENTION

The present invention comprises a simplified fluid separation method and device.

In accordance with the present invention, there is provided a fluid separation or apheresis method wherein at least one pump is utilized to draw fluid (e.g. blood) from a source (e.g. a human subject) and to move such fluid into a fluid separation device. Thereafter, the separation device is utilized to separate the fluid (e.g. blood) into at least a first blood fraction (e.g. cell concentrate) and a second blood fraction (e.g. plasma). A single weighing device is operatively connected to a first fluid fraction container (e.g. a cell bag) and a second fluid fraction container (e.g. a plasma vessel) so as to measure the combined weight of such first fluid fraction container and second fluid fraction container along with the contents thereof. Initially, the weight on the weighing device is that of the empty first fluid fraction container and the empty second fluid fraction container, and such weight may be recorded or stored. After the first and second fluid fractions have been collected in the respective containers, a second weight on the weighing device may be recorded. Such second weight includes the first and second fluid fraction containers as well as the first and second fluid fractions contained therein. Thereafter, the first fluid fraction is removed from the first fluid fraction container and reinfused into the human subject. Following such reinfusion, a third weight on the weighing device (i.e. the weight of the empty first blood fraction container and the weight of the second blood fraction container plus its contents) may be recorded. The weights recorded on the weighing device may then be utilized to calculate new flow constants for the pump(s) utilized in drawing and/or reinfusing the fluid and/or fluid fraction(s). The calibration of the pump(s) may then be adjusted in accordance with the newly calculated flow constants.

Further in accordance with the invention, weights recorded by the single weighing device may be continuously or periodically used to monitor the flow of first fluid fraction during reinfusion. The monitored weight, or change in weight, is then compared to an "expected" weight based on the expected throughput of the pump being utilized to effect such reinfusion. If the monitored weight, or change in weight, is found to differ more than an allowable amount from the "expected" weight, such is taken to be an indicator of either (a) depletion of the first blood fraction from the first blood fraction container or (b) a malfunction in the system. At such point, the reinfusion pump(s) is stopped.

Still further in accordance with the invention, there is provided an automated fluid processing or apheresis machine having at least one pump, a fluid or blood separator and a single weighing device with separate fluid fraction collection vessels (e.g. a plasma vessel and a flexible cell concentrate bag) positioned thereon. This automated machine may be utilized to carry out the method of the present invention as described herein.

Still further in accordance with the invention, an automated apheresis machine may comprise a plurality of pumps (e.g. a whole blood pump and a cell concentrate pump) which operate, in combination, to effect the withdrawal, separation and reinfusion of the blood and/or blood components. A single weighing device is utilized to simultaneously weigh at least two of the separated blood components, at various points in the procedure. The weights recorded by the single weighing device may, thereafter, be utilized to calculate actual flow constants for the pumps and/or to monitor and verify quantities or dynamics of fluid movement(s) within the machine.

BRIEF DESCRIPTION OF THE DRAWINGS

FIG. 5a is a flow diagram illustrating a plasmapheresis method in accordance with the present invention;

FIG. 5b is a continuation of the flow diagram of FIG. 5a;

FIG. 8 is a perspective view of a presently preferred blood filter/bubble trap usable as a component in the device of the present invention;

FIG. 8a is a perspective view of a portion of the blood filter/bubble trap shown in FIG. 8; FIG. 8b is a partial longitudinal sectional view through line b—b' of FIG. 8;

FIG. 8c is a cross-sectional view through line c—c' of FIG. 8;

FIG. 9a is an illustration of that which constitutes the "DRY TARE" measurement taken in accordance with the method of the present invention;

FIG. 9b is an illustration of that which constitute the "PRIMED TARE" (first cycle) measurement taken in accordance with the method of the present invention;

FIG. 9c is an illustration of that which constitutes the "EMPTY CELL BAG TARE" measurement taken in accordance with the method of the present invention;

FIG. 9d is an illustration of that which constitutes the "PRIMED TARE" (later cycles) measurement taken in accordance with the method of the present invention;

FIG. 10 is an illustration of that which constitutes the calculated predicted plasma weight ($P_{pre}$) in accordance with the method of the present invention;

FIG. 11 is an illustration of that which constitutes the POST COLLECTION WEIGHT determined in accordance with the method of the present invention; and FIG. 12 is an illustration of that which constitutes the POST REINFUSION WEIGHT determined in accordance with the method of the present invention.

DETAILED DESCRIPTION OF THE ILLUSTRATIVE EMBODIMENTS i. The System of the Present Invention

The following detailed description and the accompanying drawings are provided for purposes of illustrating certain embodiments of the present invention and are not intended to limit the scope of the invention in any way.

The present invention is particularly applicable to automated plasmapheresis equipment and, thus, will be described herein with particular reference to plasmapheresis procedures. It will be appreciated, however, that the invention is equally applicable to other fluid processing and apheresis procedures, including but not limited to, leukapheresis, thrombocytapheresis, therapeutic plasma exchange, therapeutic plasma processing, etc.

Figure 1:
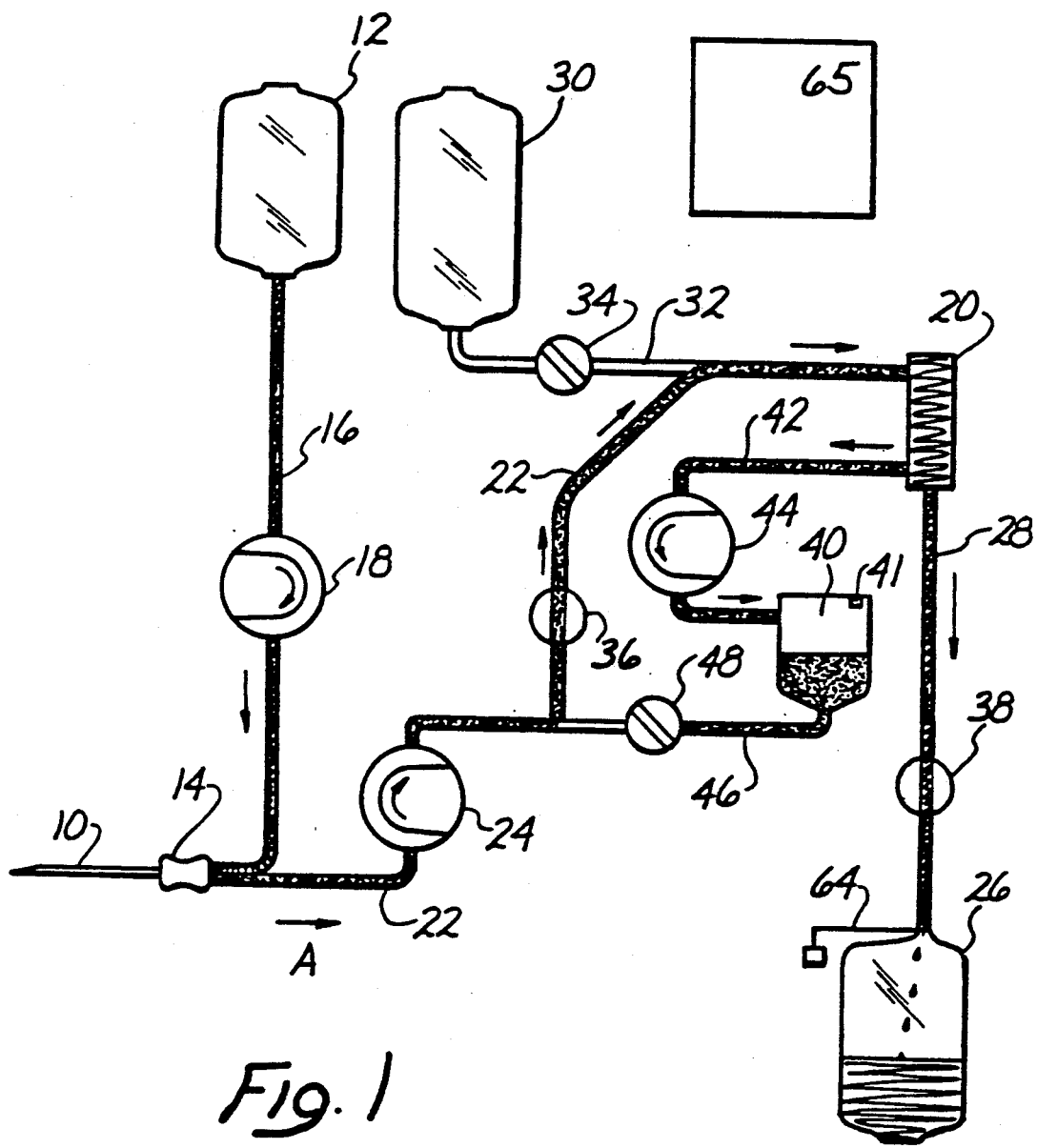
FIG. 1 is a schematic diagram of a plasmapheresis method and device of the prior art, during a typical collection cycle.
Figure 2:
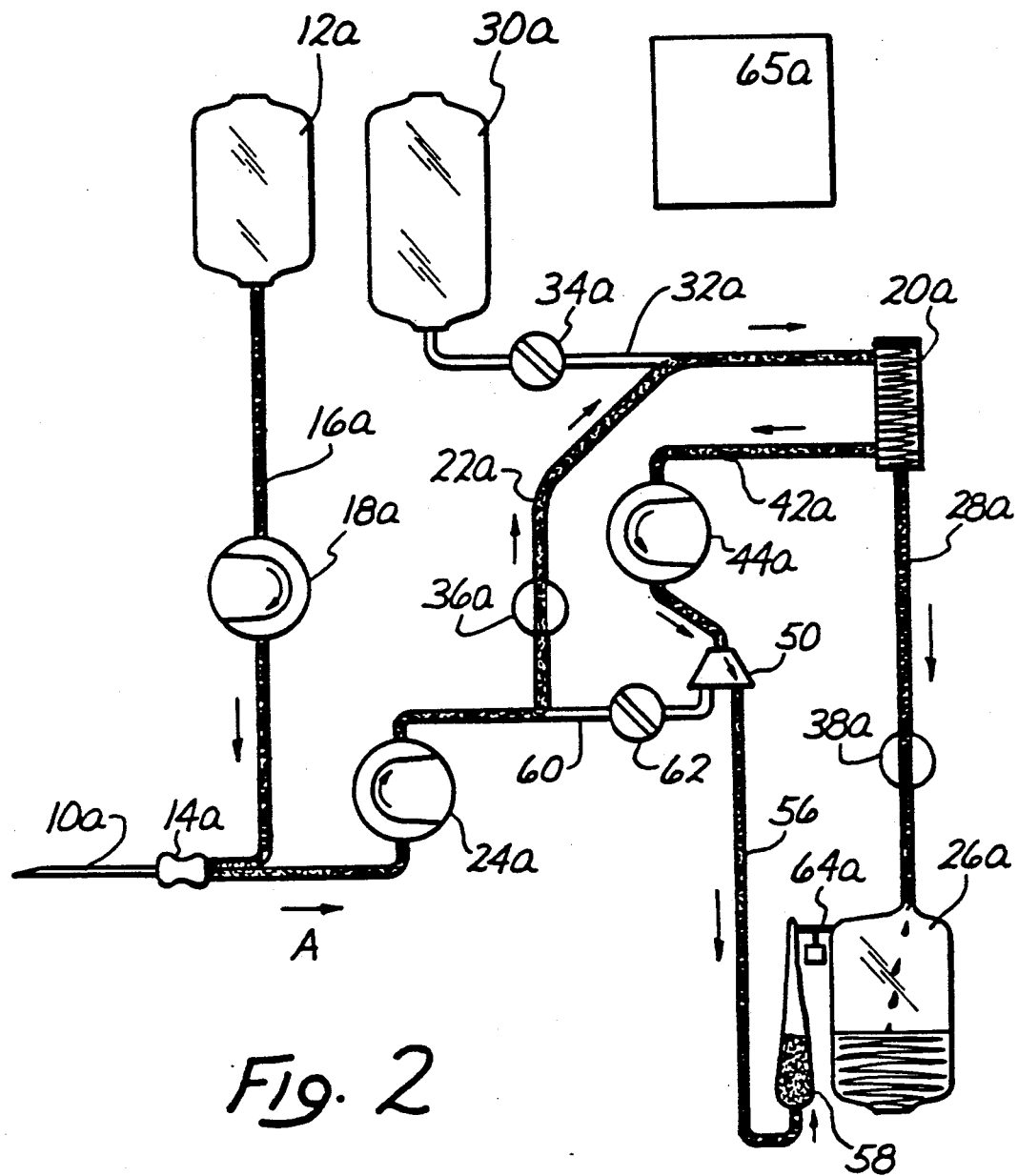
FIG. 2 is a schematic diagram illustrating a plasmapheresis method and device of the present invention, during a typical collection cycle.
Figure 3:
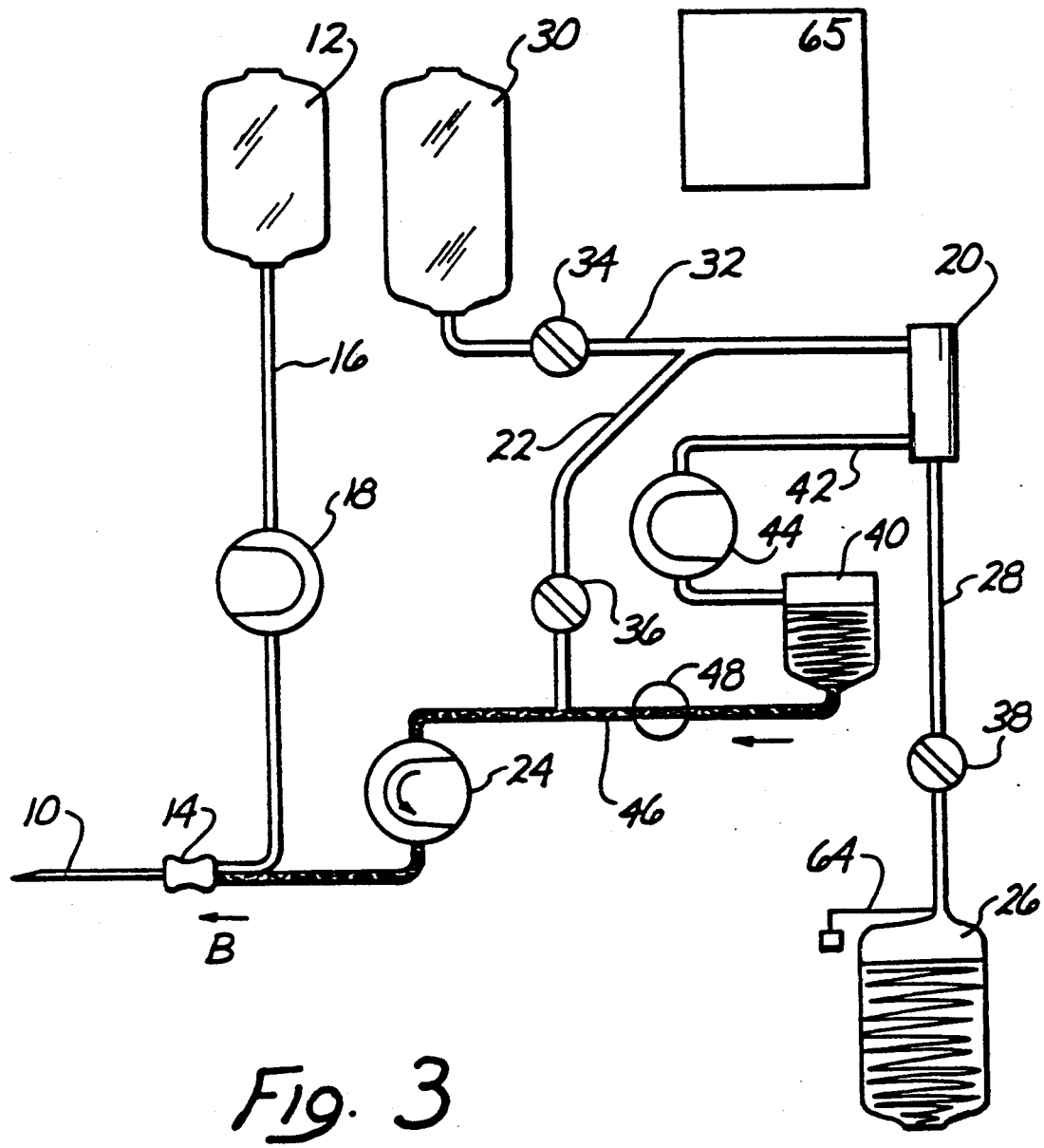
FIG. 3 is a schematic diagram illustrating a plasmapheresis method and device of the prior art during a typical reinfusion cycle.
Figure 4:
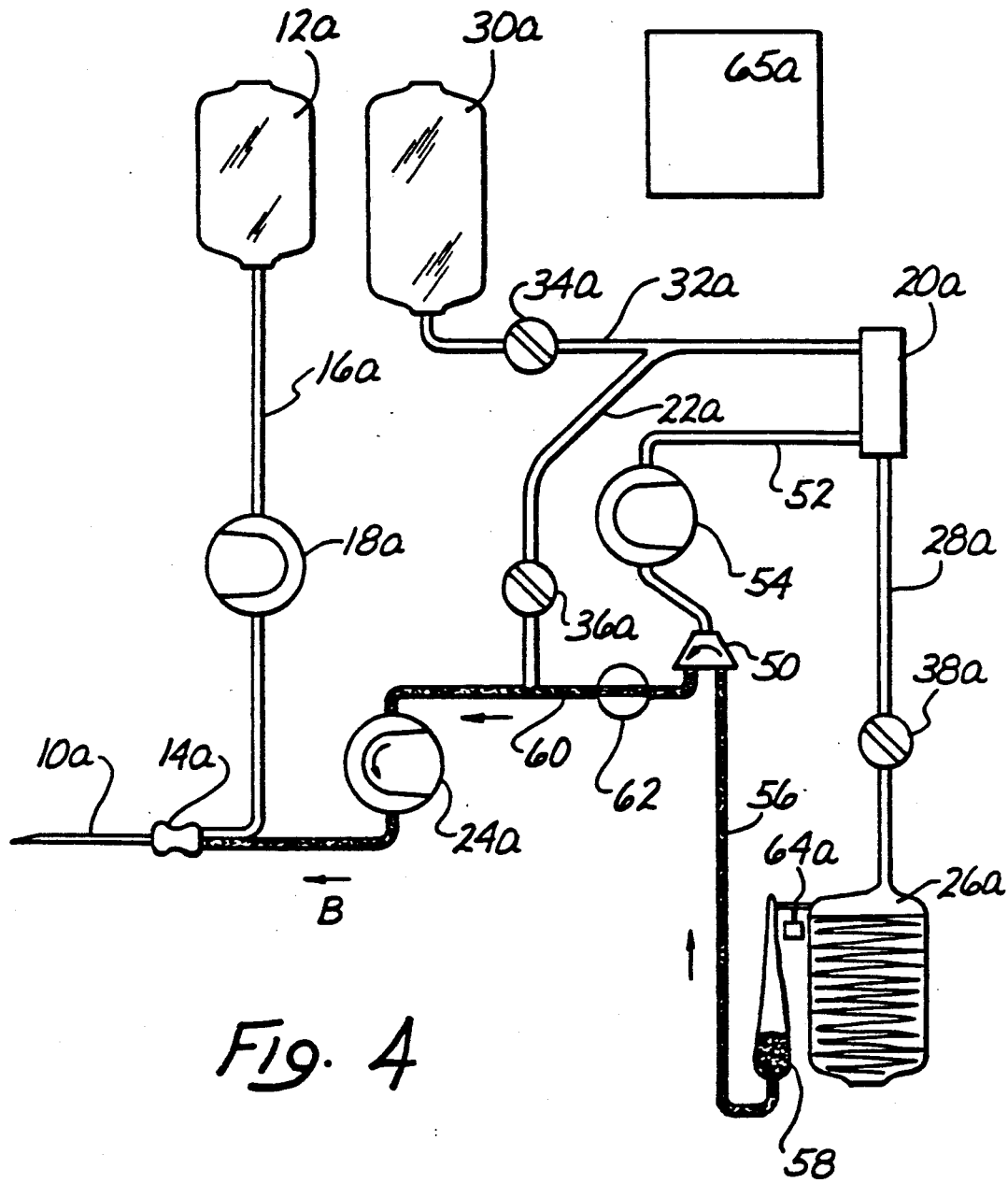
FIG. 4 is a schematic diagram illustrating a plasmapheresis method and device of the present invention during a typical reinfusion cycle.

FIGS. 1 through 4 are comparative, schematic illustrations of a prior art apheresis method and device (FIGS. 1 and 3) and an embodiment of the method and device of the present invention (FIGS. 2 and 4).

Generally, the apheresis systems of the prior art and those of the present invention incorporate certain common components. A venipuncture needle 10, 10a is percutaneously insertable into a peripheral vein of a human plasma donor. A bag or other container of anticoagulant solution 12, 12a is fluidly connected, by tube 16, 16a, to a mixing chamber 14, 14a which is proximal to needle 10.

An anticoagulant pump 18, 18a is positioned on tube 16, 16a to draw anticoagulant solution from bag 12, 12a through tube 16, 16a, into the mixing chamber 14, 14a. Anticoagulant solution entering the mixing chamber 14, 14a will join with, and will become dispersed in, blood which has been extracted proximally through needle 10.

A blood separation apparatus 20, 20a is fluidly connected to the mixing chamber 14, 14a by tube 22, 22a. A bidirectional blood pump 24, 24a, preferably a peristaltio pump, is positioned on tube 22, 22a for alternate withdrawal of blood and infusion of cell concentrate through needle 10, 10a. Movement of the blood pump 24, 24a in a clockwise direction will move blood in the direction of arrow A (withdraw), while movement of blood pump 24, 24a in a counter-clockwise direction will move fluids (e.g. cell concentrate from line 60) in the direction of arrow B, back to the human subject.

A cell pump 44, 44a is positioned on line 42, 42a to move cell concentrate out of the separation device 20, 20a at a controlled rate. Close control of the calibration of the cell pump 44, 44a is critical in that there exists strict limits on the amount of oxygen transporting red blood cells which may be held in the extracorporeal circuit at any point in time. Thus, close control of the amount of cell concentrate being pumped by the cell pump 44, 44a is necessary to ensure that such limits are not exceeded. Also, the calibration and throughput of the cell pump directly affects the transmembrane pressure within the separation device 20, 20a. If the calibration and throughput of the cell pump 44, 44a is not closely controlled, errant pressures within the separation device 20, 20a may result in hemolysis of the blood cells, incomplete separation of the blood and/or an automatic error signal and shut down of the machine. A plasma container 26, 26a is connected to the plasma outlet port of blood separator 20, 20a by way of tube 28, 28a. A saline bag or container 30, 30a is connected to blood line 22, 22a at a point near the inlet port of blood separation device 20, 20a. A saline valve 34, 34a is alternately positionable in an open position whereby flow through line 32, 32a, is permitted and a closed position whereby flow through line 32, 32a is prohibited.

A blood valve 36, 36a is positioned on blood line 22, 22a. Blood valve 36, 36a is alternately positionable in an open position whereby flow through line 22, 22a is permitted, and a closed position whereby flow through line 22, 22a is blocked.

A plasma valve 38, 38a is positioned in line 28, 28a. The plasma valve 38, 38a is alternately positionable in an open position whereby flow through line 28, 28a is permitted and a closed position whereby flow through line 28, 28a is prohibited.

In the typical apheresis machine of the prior art (FIGS. 1 and 3), a cell concentrate reservoir 40 is located remotely from the separate plasma vessel 26. Separate, discrete systems are employed to monitor the relative weights and/or volumes of a) cell concentrate collected in the cell reservoir 40 and b) plasma collected in the plasma vessel 26. As shown, the plasma vessel 26 is attached to weighing device 64, such as an electronic balance, so as to continuously monitor the weight of the plasma container 26 and its contents. The level of cell concentrate in the cell reservoir 40 is, on the other hand, often measured by a series of electronic sensors or other measuring device(s) located in or adjacent to the cell reservoir 40. Thus, the weighing device 64 and the sensors or other measuring device(s) associated to the cell reservoir 40, are separately connected to, and provide separate signals to a central computer 65, 65a. The computer 65, 65a may include an electronic microprocessor, timing and logic circuits, program memory, communication busses and power supply connections.

The cell concentrate reservoir of the prior art machine 40 (FIGS. 1, 3) is fluidly connected to the cell concentrate output port of the blood separation device 20 by way of a flexible tube 42. A cell pump 44, such as a peristaltic pump, is positioned on tube 42 so as to pump the cell concentrate from the cell concentrate outlet port of the blood separation device 20 through line 42 into the cell concentrate reservoir 40. The outlet port of cell concentrate reservoir 40 is connected to the lower portion of the blood line 22 by way of a flexible tube or line 46. Cell concentrate valve 48 is positioned on line 46. The cell concentrate valve 48 is alternately positionable in an open position whereby flow through line 46 is permitted, a closed position whereby flow through line is prohibited.

As shown in the diagrams of FIGS. 2 and 4, the system of the present invention differs from the prior art system shown in FIGS. 1 and 3 in that the concentrate outlet port of the blood separation device 20a is connected to the top inlet port of a blood filter/bubble trap 50 by way of a flexible tube or line 52. The cell pump 44a is positioned on line 42a to pump cell concentrate from the cell concentrate output port of blood separator device 20a into the top port of blood filter/bubble trap 50. Another flexible tube or line 56 connects the right side bottom port of blood filter/bubble trap 50 to a bottom fill port of cell bag 58. A left side bottom port of cell filter/bubble trap 50 is connected to a point on line 22a, as shown, by way of a flexible tube or line 60. A cell concentrate valve 62 is positioned on line or tube 60. Cell concentrate valve 62 is alternately positionable in an open position whereby flow through line 60 is permitted, and a closed position whereby flow through line 60 is blocked.

The darkened tubes and components (shown in FIGS. 1 and 2) indicate the respective flow paths of fluids within a typical prior art apheresis system during collection (FIG. 1) and reinfusion (FIG. 3).

As specifically illustrated in FIG. 1, the collection of plasma by a prior art plasmapheresis machine was generally accomplished with valves 36 and 38 in their open positions and valves 34 and 48 in their closed positions. Anticoagulant pump 18, blood pump 24 and cell pump 44 are concomitantly actuated during collection, so as to pump fluids in the directions indicated by the arrows of FIG. 1. Specifically, an anticoagulant pump 18 turns in a clockwise direction to pump dilute anticoagulant solution from anticoagulant reservoir 12, through line 16, into the mixing chamber 14 which is positioned proximal to venipuncture needle 10. Blood pump 24 rotates in a clockwise direction and operates to withdraw blood through needle 10 such that blood will become mixed with anticoagulant solution as the blood is drawn through the mixing chamber 14. Whole blood (mixed with anticoagulant solution) is then withdrawn by blood pump 24, through line 22, into the separation device 20. The separation device 20 substantially separates blood plasma from a cell concentrate which contains the formed elements of the blood (i.e. red cells, white cells and platelets). The cell pump 44 operates to withdraw the cell concentrate from the cell concentrate outlet port of blood separation device 20, through line 42 and deposits the cell concentrate in cell concentrate reservoir 40. Since valve 48 is in its "closed" position, the cell concentrate is prevented from moving past valve 48 when the device is in the depicted collection mode. Air displaced from the interior of the reservoir is vented through a hydrophobic filter/vent port 41 formed in the top of the reservoir 40. Blood plasma flowing from the plasma outlet port of the blood separation device 20 is permitted to drain through line 28 into plasma collection vessel 26.

In the device of the present invention (FIGS. 2 and 4) a single weighing device 64a, such as an electronic balance or load cell, is utilized to concomitantly weigh a) the plasma container 26a and its contents, and b) the cell concentrate bag 58 and its contents. The use of this single weighing device 64a for both the plasma container 68a and the cell bag 58 eliminates the need for a separate system for collecting and measuring the cell concentrate at a location remote from the plasma container. Also, the use of the single weighing device 64a, in accordance with the method of the present invention, provides for highly accurate measurement of the throughput, of the blood pump 24, 24a and cell pump 44, 54, thereby permitting accurate and frequent recalibrations thereof. Additionally, this invention enables continuous, redundant monitoring of the blood/cell concentrate flow during withdrawal and reinfusion by providing a continual indication of flow rate based on the changes of weight being recorded by the single weighing device 64a as the withdrawal or reinfusion occurs. The change in weight or rate of change in weight recorded by weighing device 64a is then continuously or periodically compared to the calculated flow rate or actual rotations of pump 44a. If the actual or expected flow through pump 44a differs more than a certain amount (e.g. 25%) from the flow rate indicated by the change in weight being recorded by the weighing device, such will indicate a problem with the system, such as a tubing leak, vessel fracture or improperly rigged or malfunctioning pump. Thus, this redundant, comparative flow monitoring capability provided by the single weighing device 64a, is also an advantage of the present invention. Additionally, the invention provides for the use of an inexpensive plastic cell concentrate container bag 58 and inexpensive blood filter/bubble trap 50 as opposed to the more expensive components used in some prior art devices, such as the rigid, vented cell reservoir 40 with attendant electronic (LED) volume monitoring used in the prior art system shown in FIGS. 1 and 3.

Figure 5B:
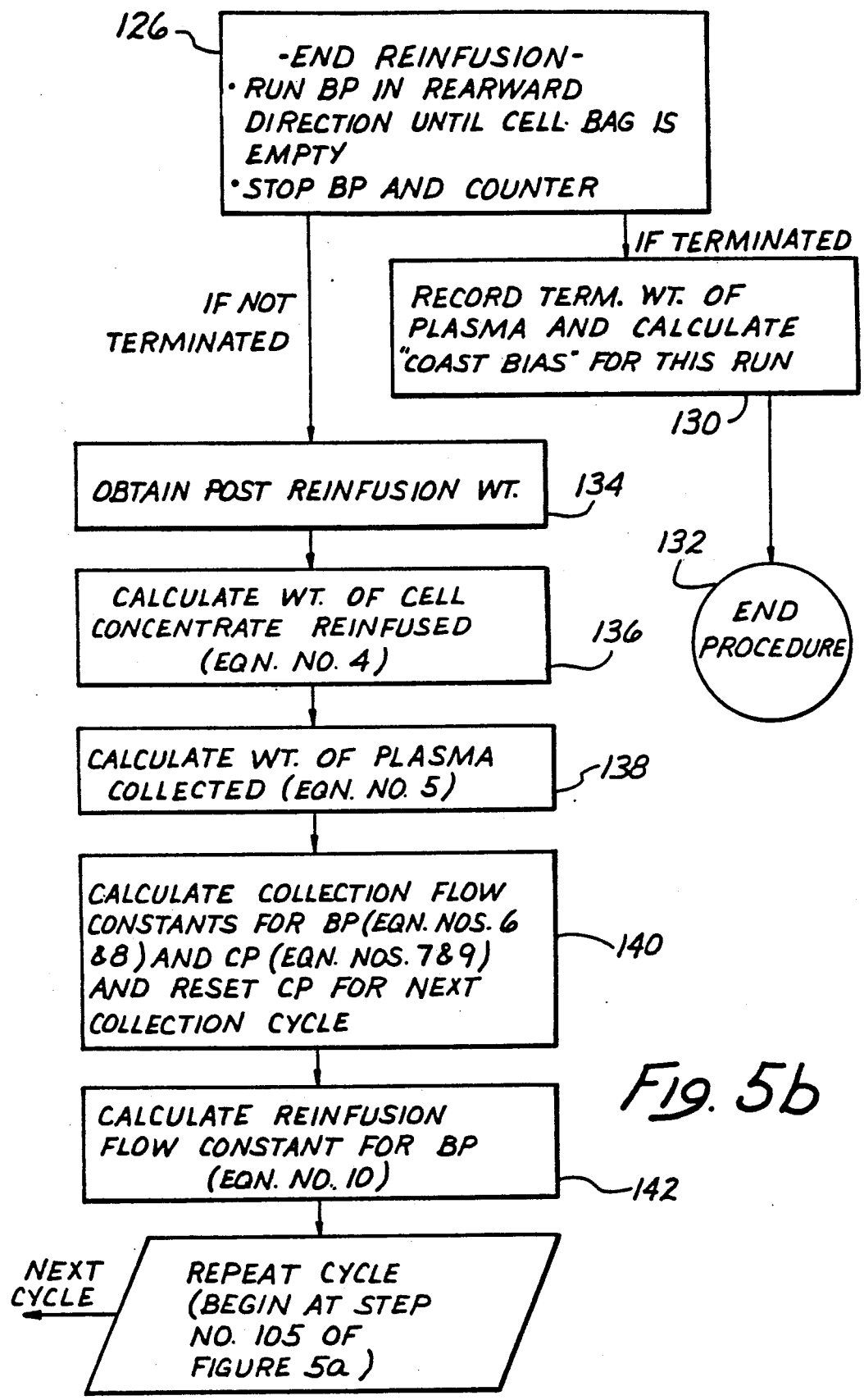

The general method by which the apheresis system of the present invention operates is shown in FIGS. 5a–5b. This method is more fully described herebelow with specific reference to the schematic diagrams of FIGS. 2 and 4.

ii. The Method of the Present Invention

Initially, the empty plasma reservoir 26a and cell concentrate bag 58 are placed on a single weighing device 84a. A "DRY TARE" is then measured by the weighing device 64a. The "DRY TARE" value is communicated to the computer 65a wherein the "DRY TARE" value is stored. The "DRY TARE" value is the combined weight of a) the empty plasma container 26a, and b) the empty cell bag 58. This "DRY TARE" step is carried out at the beginning of the procedure, prior to the initial priming of the system, as illustrated in FIG. 9a. The "DRY TARE" value is the combined weight of the empty plasma vessel 26, 26a, 234, 234a and the empty cell bag 58, 237. In subsequent cycles after the initial cycle, an "EMPTY CELL BAG TARE" 105 is determined and stored instead of the "DRY TARE" determined and stored at initiation of the first cycle. The "EMPTY CELL BAG TARE" 105 differs from the "DRY TARE" in that it includes the weight of plasma collected in previous collection cycles, as illustrated in FIG. 9c.

Thereafter, a portion of the system (e.g., the blood tube 22a, blood separator device 20a, tube 52, blood filter/bubble trap 50, tube 56 and blood bag 58) is initially primed with a quantity of anticoagulated whole blood withdrawn through venipuncture needle 10a. Such priming of the system 110 will typically result in a small amount of whole blood being disposed in the bottom of the cell concentrate bag 58. At this point, a "PRIMED TARE" is measured 112 by the weighing device 64a. The "PRIMED TARE" value is communicated to the computer 65a wherein such "PRIMED TARE" value is stored. The "PRIMED TARE" value is the combined weight of the a) empty plasma container, and b) cell bag containing the small amount of priming blood as illustrated in FIG. 9b.

After the "PRIMED TARE" has been recorded 112, an initial collection cycle is begun 114. During such collection cycle, the blood valve 36a is in its "open" position, the infusion valve 62 is in its "closed" position, plasma valve 38a is in its "open" position and blood pump 24a and cell pump 44a are operated in their respective, clockwise and counter-clockwise directions, at specifically controlled rates, as dictated by the program of the computer 65a. The set rates of the pumps 24a and 54 are calculated by the computer 65a on the basis of the desired pressures to be maintained within the attendant tubing 22, 52, 28a and the blood separation device 20a. The rate of the blood pump 24a is also determine, to some degree, in view of the volume and pressure of blood available to be withdrawn from the blood vessel of the human subject.

The total volume of blood to be withdrawn into the extracorporeal circuit in any given collection cycle is controlled by presetting the number of rotations to be made by the cell pump 44a during the next collection cycle. The numbers of rotations that the pumps 24a and 44a will undergo, in each given collection cycle, is controlled by computer 65a on the basis of a preset "pump flow constant" for each pump (BP and CP). The desired number of rotations for any given collection cycle is generally determined on the basis of the following equation:

Equation No. 1

$$\frac{\text{Weight of Material Pumped (g)}}{\text{Sp.Gr. of Material (g/ml)}} = \frac{\text{Counted Number of Pump Revs. (Rev.)}}{\text{Flow Constant (Rev./ml)}}$$

To control the volume to be pumped during the first or start-up collection cycle (step 114–116), the desired rotations for the cell pump 44a will be preset by the computer 65a on the basis of an "initial" flow constant for each pump. Thereafter, for each repetitive collection cycle, an "adjusted" flow constant will be determined and stored in the computer 65a. Each such "adjusted" flow constant will be based on actual measurements made during the previous collection cycle. Such frequent adjustment of the desired rotations of the blood pump and cell pump helps to insure that accurate fluid volumes are maintained throughout the procedure.

The collection is accomplished by running the blood pump 24a and cell pump 54 in their respective "collection" directions or modes. Typically, such will require that the blood pump 24a be rotated in a clockwise direction while the cell pump 54 be rotated in a counter-clockwise direction. Typically, the cell pump 44a is utilized to precisely gage and control the amount of red cells withdrawn in a single collection cycle and the blood pump 24a continues to run in conjunction with the cell pump 44a until the cell pump is stopped (i.e. where it has undergone a present number of rotations. Thus, in any collection cycle prior to the final collection cycle of a given procedure, the cell pump 54 will undergo a predetermined number of rotations as preset in the computer 65a or as selected or overridden by the operator. The present number of rotations will achieve a precalculated quantity of cell concentrate pumped by cell pump 44a. Such precalculated quantity of blood cell concentrate withdrawal is generally related to a specific weight of cell concentrate contained within the cell bag 58 and is below the maximum allowable extracorporeal red cell volume permitted by applicable government regulations.

In order to insure that the maximum allowable plasma collection is not exceeded, it is desirable to continuously or periodically calculate the current predicted or calculated plasma wt. ($P_{pre}$) and to continuously, or at discrete time points during each collection cycle, compare such predicted plasma volume to the maximum allowable volume of plasma withdrawal ($P_{max}$) 116. The $P_{max}$, in most instances, is determined from generally published data tables or nomograms, based on the height and/or weight of a generally healthy blood donor and in accordance with governmental regulations. In certain therapeutic instances, however, the $P_{max}$ will be determined and set by the operator or medical practitioner taking into account the general health of the patient and/or other facts relating to the therapeutic procedure being performed.

In a preferred embodiment of the present invention, the computer 65a continuously monitors the $P_{pre}$ in comparison to $P_{max}$. The predicted plasma ($P_{pre}$) is determined by the following formula:

Equation No. 2

Primed Cell Bag$\Delta$ = Primed Tare − Empty Cell Bag Tare

Equation No. 3

$P$ = Current Weight − Dry Tare − Primed Cell Bag$\Delta$ − Current Cell$\Delta$ + Coast Bias When $P_{pre}$ is determined to equal $P_{max}$, the collection is immediately terminated by the computer 65a and the device moves directly into the final reinfusion cycle of the procedure, as will be fully described hereinafter.

In a typical prefinal collection cycle (a full collection cycle which yields a final volume of plasma collected which is less than $P_{max}$) prior to the final collection cycle during which the procedure is terminated, the end of collection will be marked by a weight of red cell concentrate within the cell bag 58 and an attendant weight of separated plasma within the plasma container 26a. After the particular collection cycle has been ended 118, the weigher 64a will take a "post-collection weight" 122, as illustrated in FIG. 11 and will transmit such weight to the computer 65a wherein it will be stored. The "post-collection weight" 122 is the combined weight of a) the plasma container plus all plasma contained therein, and b) the cell bag plus all cell concentrate (and any priming blood) collected therein plus any priming blood, primed cell bag$\Delta$, 324, contained therein.

After the "post-collection weight" has been recorded 122, the blood valve 36a will move to its "closed" position and reinfusion valve 62 will move to its "opened" position. The blood pump 24a will then be operated in its counter-clockwise direction to effect reinfusion of the cell concentrate (and/or any priming blood) from the cell bag 58, through tube 56, through blood filter/bubble trap 50, through tube 60, through mixing chamber 14a, and distally through needle 10a, into the blood vessel of the human donor. It is desirable that such reinfusion cycle effect complete reinfusion of all cell concentrate (and/or priming blood) contained in the cell bag 58a. Thus, the computer 65a may be capable of continuously or periodically monitoring the flow of fluid through the reinfusion system in order to detect when the cell bag 58a has been fully emptied and to automatically stop the counter-clockwise movement of the blood pump 24 at such point. The actual number of revolutions made by the blood pump 24 during each reinfusion of cell concentrate is counted 128 and stored in computer 65a. If a subsequent collection cycle is to be completed, (i.e. if the volume of plasma collected thus far has not reached $P_{max}$), then the weighing device 64a will determine and store 134 a "post-reinfusion weight". The "post-reinfusion weight" is the combined weight of a) the plasma container plus all plasma contained therein, and b) the empty cell bag.

After the "post-reinfusion weight" has been stored 134 in the computer 65a, the computer 65a will proceed to calculate the "weight of cells reinfused" 136. The "weight of cells reinfused" is determined on the basis of the following formula:

Equation No. 4

$$\text{Wt. of Cell Concentrate Reinfused(g)} = (\text{Post-Coll.Wt.(g)}) - \text{Post-Reinf.Wt.(g)})$$

Additionally, the computer will calculate the "weight f actual plasma collected" 138 as of the end of the just-ended collection cycle. The "weight of actual plasma collected", "wt. of blood pumped during collection" and the wt. of cell concentrate pumped during collection" are then calculated by the following equations nos. 5, 6, and 7:

Equation No. 5

$$\frac{\text{Wt. of Plasma}}{\text{Collected (g)}} = \frac{\text{Post-Reinfusion}}{\text{Wt. (g)}} - \frac{\text{EMPTY CELL}}{\text{BAG TARE (g)}}$$

Equation No. 6

$$\frac{\text{Wt. of Blood Pumped during Collection Cycle (g)}}{} = \frac{\text{Post-Collection Wt. (g)}}{\text{(see FIG. 11)}} - \frac{\text{PRIMED TARE (g)}}{\text{(see FIG. 9d)}}$$

Equation No. 7

$$\begin{aligned}\text{Wt. of Cell Concentrate} \\ \text{Pumped During Collection} \\ \text{Cycle (g)}\end{aligned} = \frac{\text{Post Collection Wt. (g)}}{\text{(see FIG. 11)}} -$$

$$\frac{\text{Post Reinfusion Wt. (g)}}{\text{(see FIG. 12)}} - \text{PRIMED CELL BAG } \Delta$$

The computer 65a will also calculate new collection flow constants for the blood pump 24a and cell pump 44a. Also, the computer 65a will automatically, on the basis of such new flow constants, reset the desired number of rotations for the blood pump and cell pump for the next collection cycle. Such resetting of the desired pump rotations prior to each collection cycle serves to ensure that during the next collection cycle, there will be accurate control of the volumes of fluids pumped by the blood pump 24a and cell pump 44a.

The calculation of the collection flow constants for the blood pump and cell pump are based on the following equations nos. 8 and 9:

Equation No. 8

$$\begin{aligned}\text{Blood Pump} \\ \text{Collection Flo.Con.} \\ \text{(Rev/ml)}\end{aligned} = \frac{\text{Sp.Gr. of Blood (g/ml)}}{\text{Wt of Blood Pumped (g)}} \times \begin{aligned}\text{No. of Pump} \\ \text{revs. during} \\ \text{collection} \\ \text{(Revs)}\end{aligned}$$

Equation No. 9

$$\begin{aligned}\text{Cell Pump} \\ \text{Collection Flo.Con.} \\ \text{(Rev/ml)}\end{aligned} = \frac{\text{Sp.Gr. of Cell (g/ml)}}{\text{Wt. of Cell Concent. Pumped (g)}} \times \begin{aligned}\text{No. of Pump} \\ \text{revs. during} \\ \text{collection} \\ \text{(Revs)}\end{aligned}$$

The weight of cells reinfused will subsequently be utilized in the calculation of a revised reinfusion flow constant for the blood pump 24a by application of Equation 1 and the newly calculated reinfusion flow constant for such pump will be reset in the computer for subsequent reinfusion cycles.

The calculation of the reinfusion flow constant for the blood pump is based on the following formula:

Equation No. 10

$$\begin{aligned}\text{Blood Pump} \\ \text{Feinfus. Flo.Con.} \\ \text{(Rev/ml)}\end{aligned} = \frac{\text{Sp.Gr. of Cell Conc. (g/ml)}}{\text{Wt. of Cell Conc. Reinfused (g)}} \times \begin{aligned}\text{No. of Pump} \\ \text{revs. during} \\ \text{Reinfusion (Revs)}\end{aligned}$$

After the new flow constants have been calculated and stored in computer 65a, and, the desired numbers of rotations of the cell pumps 44a has been adjusted (steps 140 and 142), a new collection cycle is begun. Steps 105-142 are repeated until such time as the computer 65a determines, during step 116 (i.e. monitoring of $P_{pre}$ versus $P_{max}$) that, the $P_{pre}$ is equal to $P_{max}$. When it is determined that $P_{pre}$ equals $P_{max}$, the collection is automatically terminated by the computer 65a, and the final reinfusion step is carried out.

After the final reinfusion step has been completed, the actual total amount of plasma collected will be determined by the weighing device 65a. Such Total Plasma Collected (Actual) will be stored by the computer 65a. The Total Plasma Collected (Actual) is determined by the following formula:

Equation No. 11

$$\begin{aligned}\text{Total Plasma Collected (Actual)} \\ \text{(g)} = (\text{Post-Reinfusion Wt. (g)}) - \text{DRY TARE (g)})\end{aligned}$$

iii. A Specific Plasmapheresis Machine Embodiment of The Present Invention

In accordance with the general system and method described above, the following detailed description of a specific plasmapheresis machine embodiment of the present invention is provided.

A blood line 180, 180a is fluidly connected to a venipuncture needle which resides within a peripheral vein of a human donor (not shown). The proximal end of the blood line 180, 180a bifurcates into a left venous pressure transducer line 182, 182a and a right blood pump tube 184, 184a. The left venous pressure transducer line is connected to a venous pressure transducer located within the housing 200 so as to provide to the computer (not shown) continual or discrete monitoring of the positive or negative pressure within the blood line 180, 180a. The blood pump tube 184 is operatively positioned within a peristaltic blood pump 186, 186a. The opposite end of blood pump line 184a is concomitantly connected, by way of a Y connector, to a reinfusion line 188, 188a and a first separator feed line 190, 190a bifurcates into a second separator feed line 192, 192a and a transmembrane pressure transducer line 194, 194a. The transmembrane pressure transducer line 194, 194a is connected to a transmembrane pressure transducer (not shown) which, in turn, is connected to the system computer (not shown) such that the computer may continuously or discretely monitor the junction of the first separator feed line 190, 190a and the second separator feed line 192, 192a.

Figure 6:
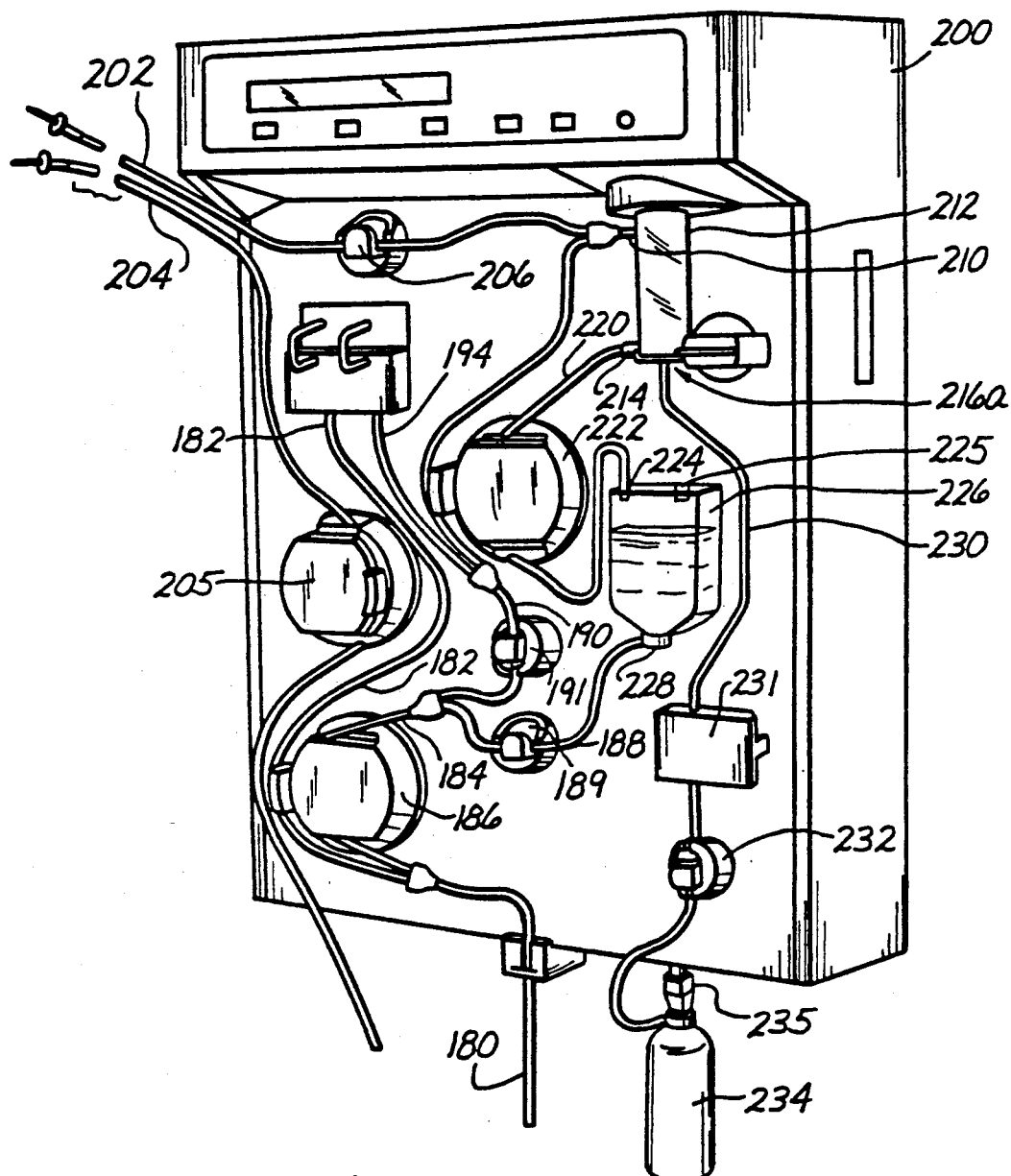
FIG. 6 is a frontal perspective view of an automated plasmapheresis machine of the prior art.
Figure 7:
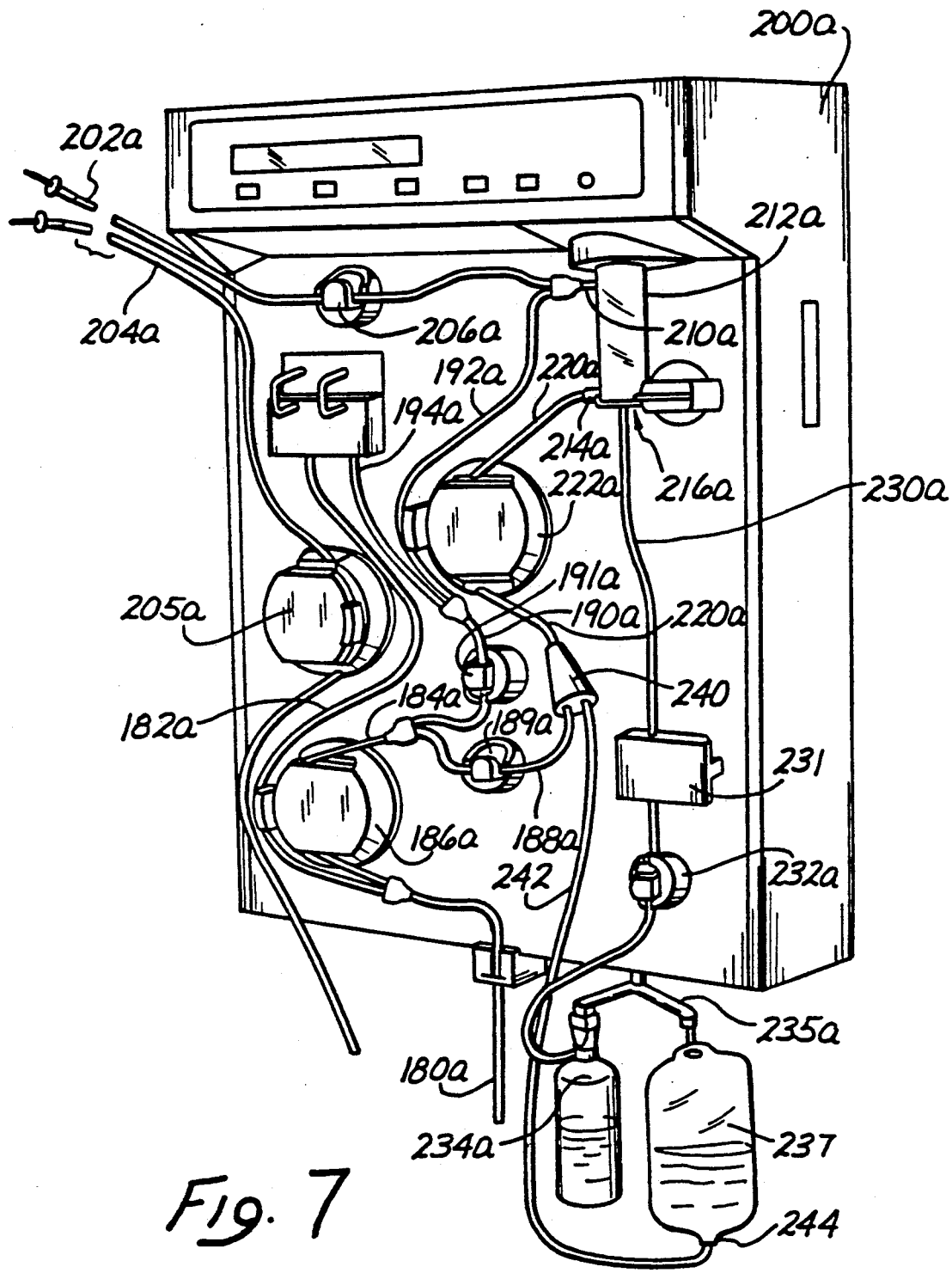
FIG. 7 is a frontal perspective view of an automated plasmapheresis machine of the present invention.
Figure 7A:
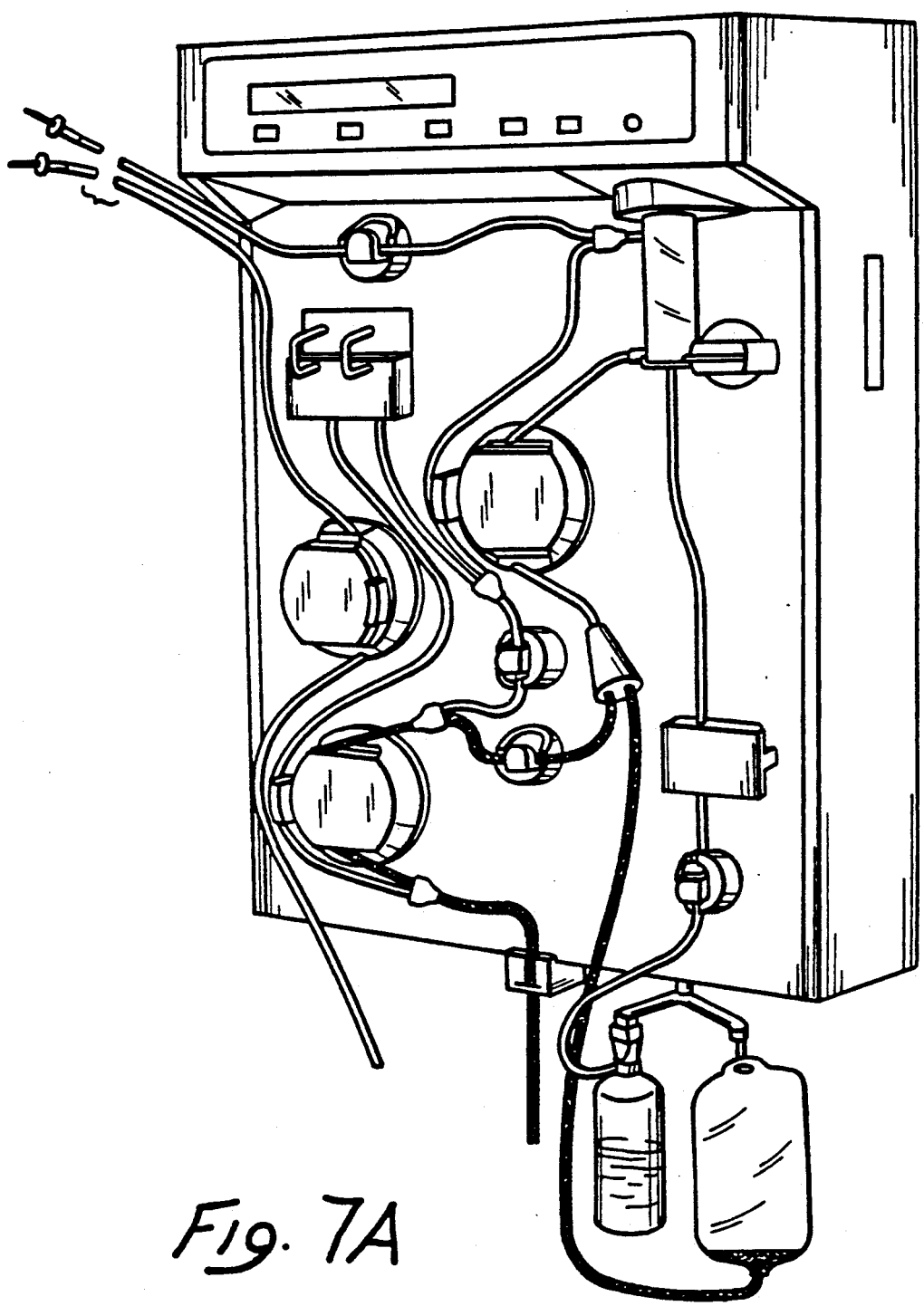
FIG. 7a is a frontal perspective view of an automated plasmapheresis machine of the present invention, with darkened areas showing the portions of the machine which contain fluid during the initiation of a priming cycle.
Figure 7B:
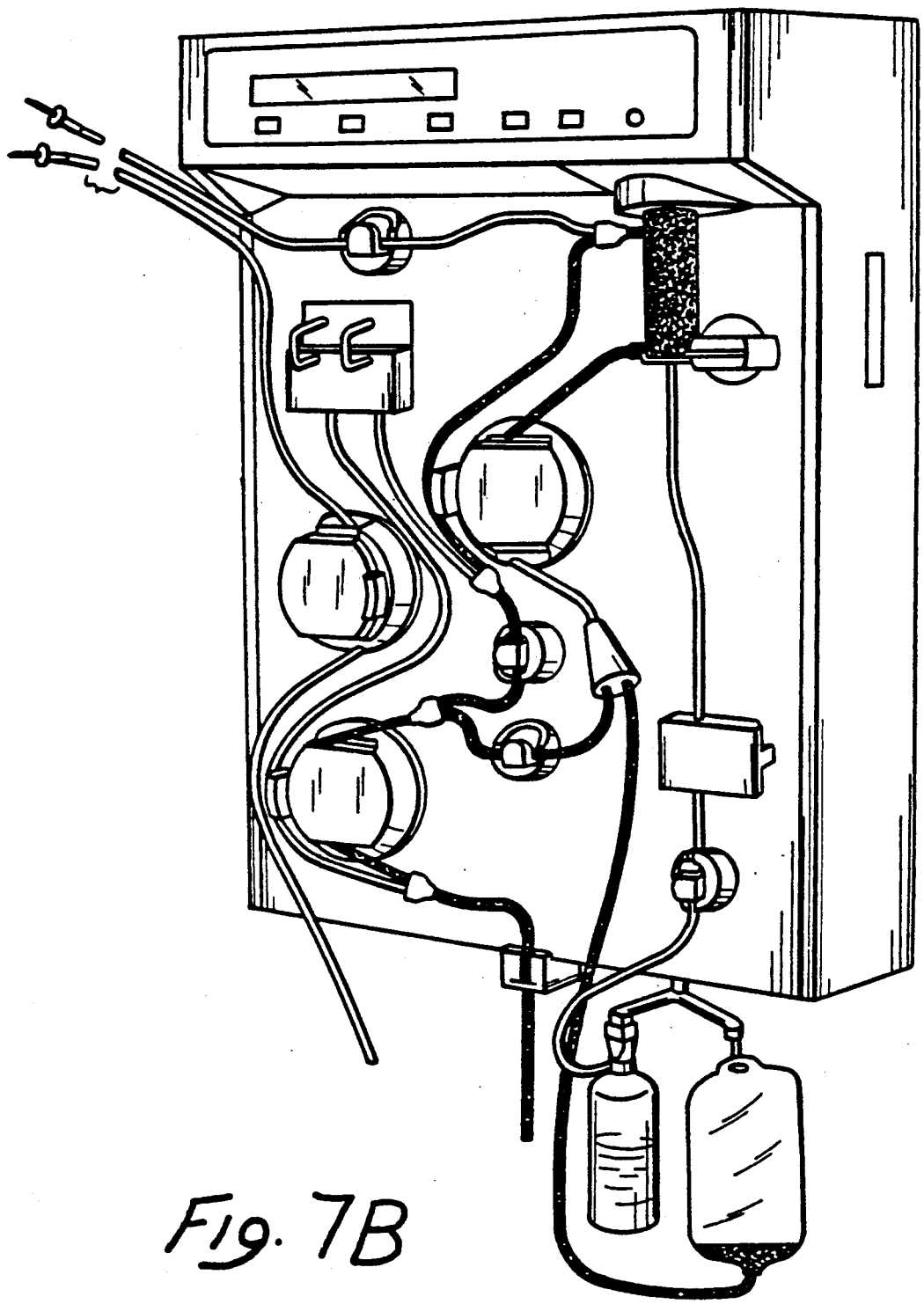
FIG. 7b is a frontal perspective view of a plasmapheresis machine of the present invention with darkened areas showing the portions of the machine which contain fluid at the end of a priming cycle.
Figure 7C:
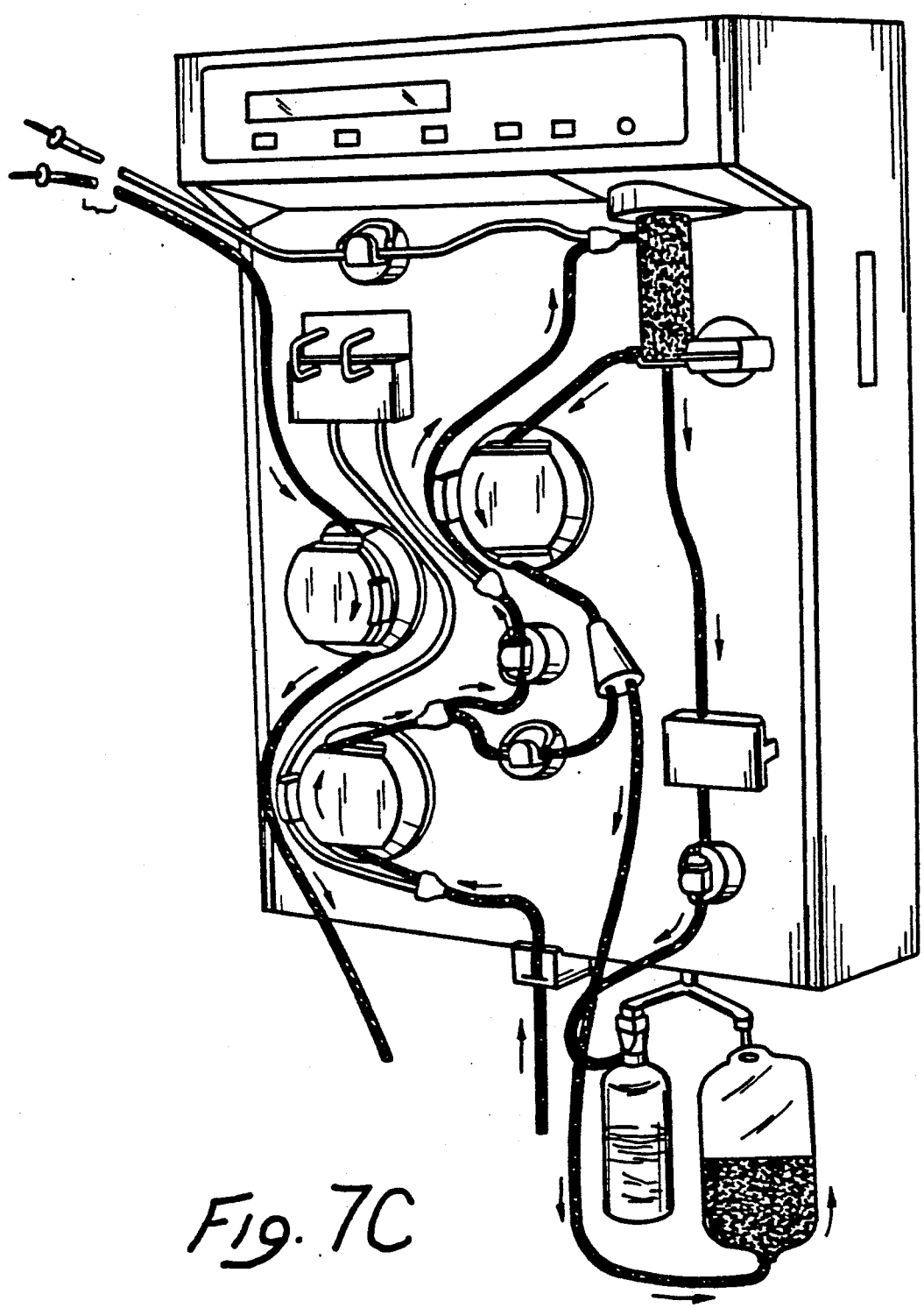
FIG. 7c is a frontal perspective view of a plasmapheresis machine of the present invention with darkened areas showing the portions of the machine which contain fluid during the beginning of a collection cycle.
Figure 7D:
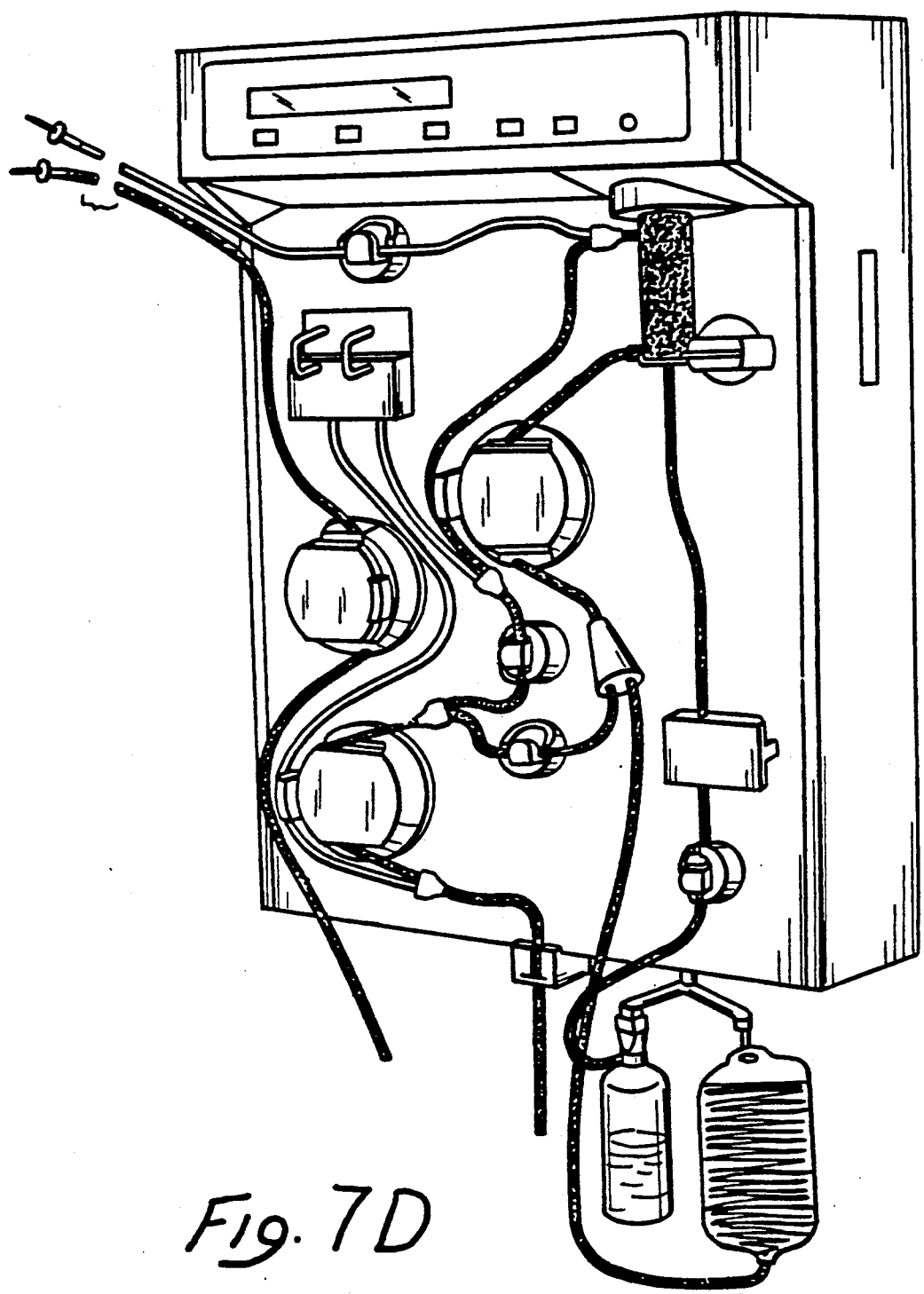
FIG. 7d is a frontal perspective view of a plasmapheresis machine of the present invention with darkened areas showing the portions of the machine which contain fluid at the end of a collection cycle.
Figure 7E:
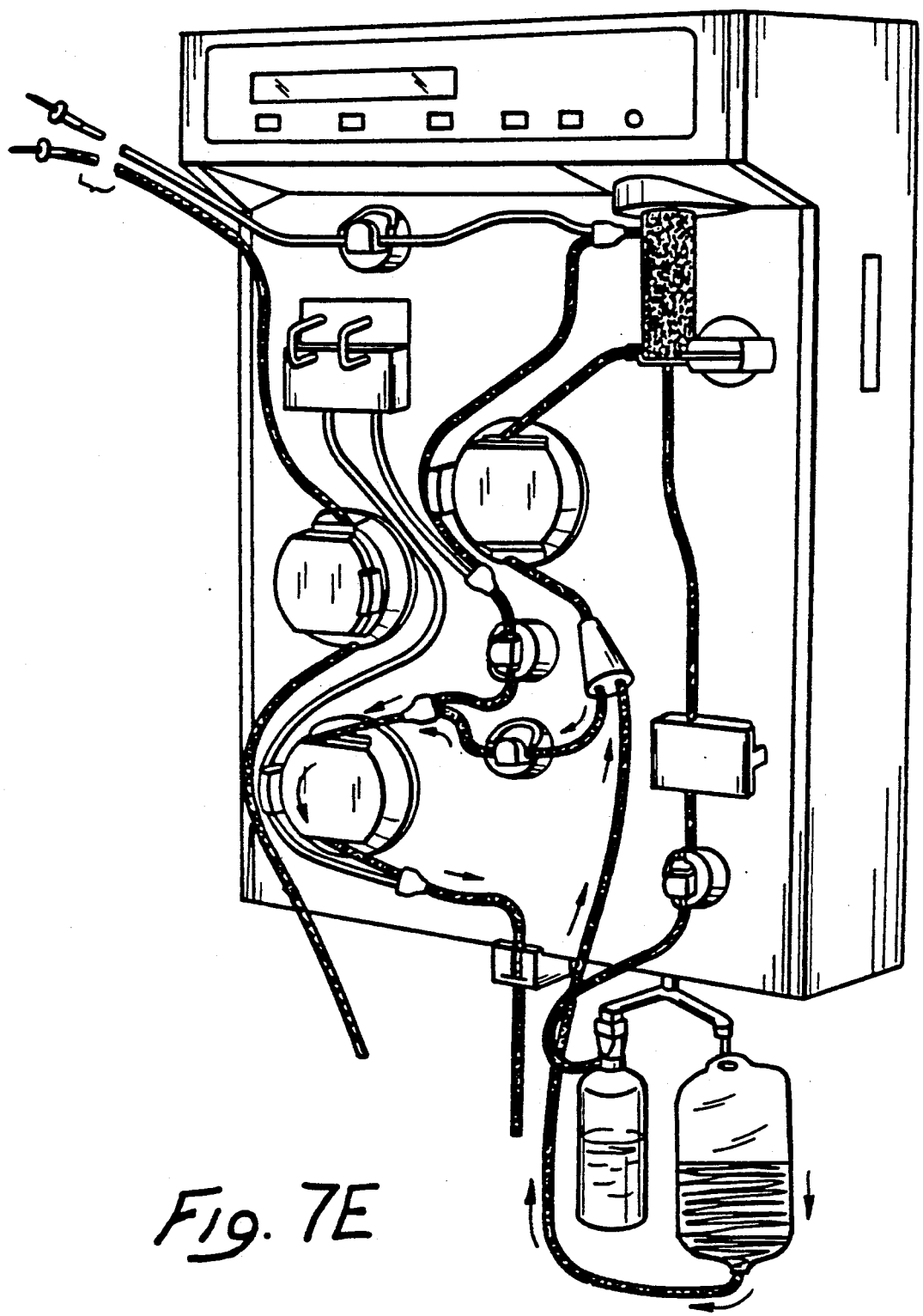
FIG. 7e is a frontal perspective view of a plasmapheresis machine of the present invention with darkened areas showing the portions of the machine which contain fluid during the beginning of a reinfusion cycle.
Figure 7F:
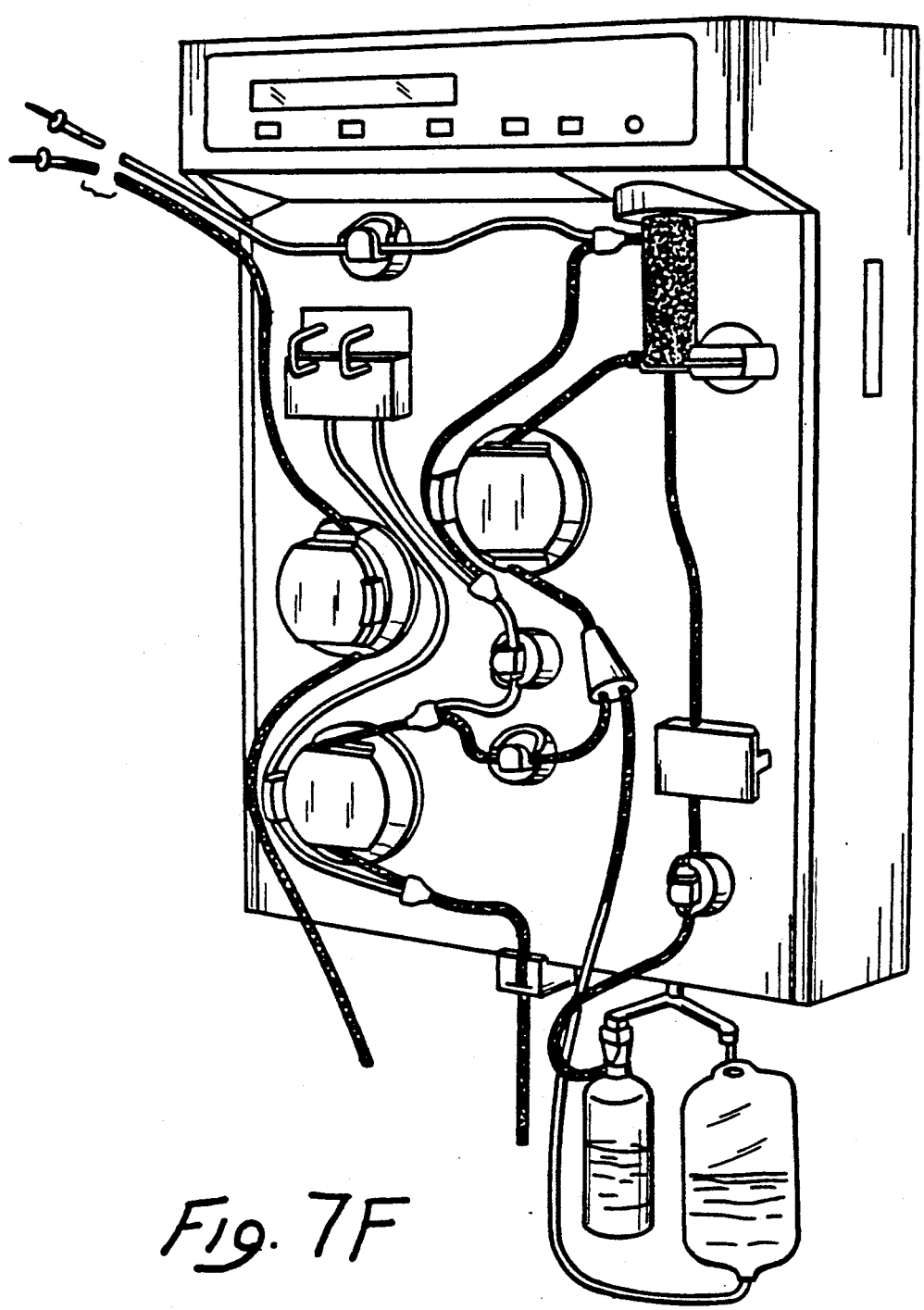
FIG. 7f is a frontal perspective view of a plasmapheresis machine of the present invention with darkened areas showing the portions of the machine which contain fluid at the end of a reinfusion cycle.

A presently preferred, automated plasmapheresis machine of the present invention is shown in FIGS. 7-7f. FIG. 6 shows a similar machine of the prior art, which does not incorporate the method or device of the present invention.

Referring to FIGS. 6 and 7, the prior art machine (FIG. 6) and the machine of the present invention (FIG. 7) share certain common components. Both of these machines comprise a housing 200, 200a wherein a central computer, wiring, electrical connections and other general components of the device (all not shown) are mounted. On the frontal surface of the housing 200, 200a, there is provided a system of tubes, pumps, reservoirs and components for effecting the desired a) withdrawal, b) separation, and c) reinfusion of blood and/or blood components. Generally, a saline line 202, 202a leads from an attendant bag or container of physiological 0.9% saline solution and an anticoagulant line 204, 204a leads from an attendant bag or container of anticoagulant solution. The saline line 202, 202a passes through a power actuated clamp 206, 206a and is connected to a Y adaptor 208, 208a. The opposite side of the Y adaptor 208, 208a is concomitantly connected to the inlet port 210, 210a of a blood separation device 212, 212a. The blood separation device may consist of any type of device capable of effectuating the desired separation of blood constituents. In a preferred embodiment, separation device 212, 212a comprises a disposable, rotational plasma separator having an internal rotatable membrane which is driven rotationally by an external magnetic motor drive (not shown). Such rotation of the inner membrane causes blood plasma to separate from the cell concentrate (a combination of red blood cells, blood white cells, platelets and a small amount of plasma). The cell concentrate flows out of the separation device 212, 212a through cell concentrate outlet port 214, 214a. The plasma flows out of the separation device 212, 212a through plasma outlet port 216, 216a.

A concentrated cell line 220, 220a is connected to the cell concentrate outlet port 214, 214a of the blood separation device 212, 212a. The concentrated cell line 220, 220a is mounted within a peristaltic cell pump 222, 222a. the peristaltic cell pump 222, 222a may be substantially identical to the previously described blood pump 186, 186a, or may comprise any other type of pump capable of effecting the desired movement of cell concentrate through concentrated cell line 220, 220a.

In the prior art device (FIG. 6), the concentrated cell line 220 carries cell concentrate from the blood separation device 212, through cell pump 222 and into the inlet port 224 of a rigid cell collection reservoir 226 having a capacity of approximately 300 milliliters. Such 300 ml capacity allows adequate extra space in the cell bag 237 when a usual collection amount limit of 180 ml of cell concentrate is observed. A cell concentrate outlet 228 is located at the bottom of the cell concentrate reservoir 226. The cell concentrate reinfusion line 188 is connected to the cell concentrate outlet 228 of the cell concentrate reservoir 226 so as to permit reinfusion of the cell concentrate into the human donor when the clamp 189 is open, clamp 191 is closed and the blood pump 186 is operated in its "reinfusion" direction (counter-clockwise). Also on the device of the prior invention (FIG. 6) a plasma line 230 extends downwardly from the plasma outlet port 216 of the blood separation device 212, passing through plasma clamp 232 and leading directly into the top of plasma collection vessel 234.

In contrast, the device of the present invention (FIG. 7) is configured so as to eliminate the need for a rigid cell reservoir and to collect the cell concentrate in a low cost flexible cell bag 236 which hangs from the same weighing device 235a as the plasma collection vessel 234a. Also, in the device of the present invention (FIG. 7) the concentrated cell line 220a is connected to one of the inlet/outlet ports of a blood filter/bubble trap 240. The blood filter/bubble trap 240 contains a screen or quantity of fibrous filtration material so as to trap bubbles, foreign objects, emboli, etc. (A specific preferred embodiment of the blood filter/bubble trap 240 is shown in FIGS. 8a through 8d and will be more fully described hereinafter.)

Also fluidly connected to the blood filter/bubble trap 240, opposite the inlet of the concentrated cell line 220a is a lower cell line extension 242. Such lower cell line extension 242 fluidly connects the blood filter/bubble trap 240 to the inlet/outlet port 244 positioned at the bottom of the cell collection bag 237.

A preferred mode of operation of the device shown in FIG. 7 is illustrated in FIGS. 7a through 7f. Specifically, FIG. 7a shows a preferred plasmapheresis machine of the present invention during the initial priming of the system. Such priming of the system is effecting by closing clamp 191a, opening clamp 189a and operating blood pump 186a in its "collection" direction (clockwise) while anticoagulant pump 205a operates relatively slowly in its operative direction (clockwise). The combination of such will result in withdrawal of whole blood (containing a small amount of anticoagulant) through the blood line 180a, blood pump line 184a, opening clamp 189a, through blood filter/bubble trap 240, down the lower cell line 242 and into the very bottom of the cell bag 237. This initial priming step is illustrated by the darkened and shaded areas shown in FIG. 7a. Generally, it is predetermined, based on the calculated dead space of the tubing and components, that approximately 32 ml of whole blood must be pumped by the blood pump in order to effect this initial priming step and to bring whole blood through to the bottom of the cell bag 237. Thus, the computer (not shown) signals the blood pump 186a to rotate in a clockwise direction. The blood pump 186a stops after a mass of 12 grams is detected on the weighing device 235a, as generally provides for initial priming of the lower portion of the system as shown in FIG. 7a.

After the initial priming step has been completed, the device moves on to a secondary priming step known as the "filter prime". The "filter prime" step is illustrated by the darkened and shaded areas in FIG. 7b. During the filter prime step, the clamp 191a is opened, clamp 189a is allowed to remain open, and the blood pump 186a is operated in its "collection" direction (clockwise) for a sufficient number of rotations to pass whole blood upwardly through line 192a and to generally fill the concentrated cell line 220a, and the remainder of blood filter/bubble trap 240. This will also result in the flow of some additional whole blood into the lower concentrated cell line 242 and the entry of a slight additional amount of blood into the bottom of the cell bag 237.

Based on the initial, empirically determined or otherwise chosen pump flow constants, the blood pump 186a and the cell pump 222a are commanded by the computer (not shown) to pump sufficient amounts of blood to fill the tubes, blood separator and blood filter/bubble trap, as shown in FIG. 7b. The computer (not shown) permits the blood pump 186a to undergo a preset number of revolutions determined to deliver that desired volume of blood and thereby effecting the desired filter prime without aspirating more than the necessary amount of blood from the patient.

After the "filter prime" step has been completed, the "PRIMED TARE" step 112 as illustrated in FIG. 9d, is carried out. Thereafter, the initial collection cycle 114 is begun.

The collection step, as applied to the presently preferred device, is illustrated in FIG. 7c. During collection, the anticoagulant pump 205a, blood pump 186a and cell pump 222a are all operative in their "collection" directions. Valve 191a is opened and valve 189a is closed. Whole blood, along with a small amount of anticoagulant solution, is drawn by blood pump 186a, through the attendant tubing, into the blood separation device 212a.

Plasma clamp 232a is opened and cell pump 222a operates to withdraw cell concentrate 220a from the blood separation device 212a. The cell concentrate passes through blood filter/bubble trap 240, down the lower cell concentrate line 242 and is collected in the cell bag 237. It will be appreciated that, while the collection process is continuing, the computer may continually monitor the plasma predicted ($P_{pre}$) versus plasma maximum ($P_{max}$) in accordance with step 116 of the inventive method (FIG. 3a). If, at any point, the $P_{pre}$ becomes equal to $P_{max}$, the computer will immediately stop the blood pump 186a, anticoagulant pump 205a, and cell pump 222a, thereby terminating the collection at $P_{max}$. The device will, upon detection of $P_{pre}$ equals $P_{max}$, move into reinfusion mode in accordance with step 124 of the inventive method (FIG. 3a). However, if $P_{pre}$ does not become equal to $P_{max}$ during the collection cycle, that collection cycle will be permitted to continue to full completion (e.g. collection of 180 milliliters of cell concentrate) where the cell pump 222a has undergone its preset number of rotations based on the precalculation of necessary rotations to obtain the desired amount (e.g. approximately 180 milliliters) of cell concentrate in the cell bag 237. When the cell pump 222a has undergone its preset number of rotations, the computer will stop the movement of all pumps 184a, 205a, 222a, thereby ending that collection cycle. Of course, during the collection, the computer will continually monitor the instant predicted plasma volume ($P_{pre}$) and will continuously or periodically compare $P_{pre}$ to the maximum allowable plasma volume, in accordance with step 118 of the inventive method (FIG. 3a).

The end of the collection cycle is illustrated in FIG. 7d.

Prior to beginning reinfusion, the weighing device 235a will measure the "post-collection weight" and such value will be stored in the computer. Thereafter, the device will begin reinfusion of the cell concentrate into the donor.

Reinfusion of the cell concentrate is effected by blood pump 186a in its "reinfusion" direction (counter-clockwise) until the entire amount of cell concentrate contained in the cell bag 237 has been reinfused into the human donor. In a preferred embodiment, the computer will monitor the flow of cell concentrate through the device in order to determine when the dynamics of reinfusion flow indicate that the entire volume of red cell concentrate (approximately 180 ml) has been reinfused. This may be achieved by continually monitoring the rate at which the weight on weighing device 235a changes with respect to blood pump flow rate and determining from the detected change in weight on weighing device 235a, when the cell bag 237 has been emptied by applying the function, such as:

$$2 \text{ g} < \text{Mag} \left| \begin{array}{c} \text{Current weight on} \\ \text{weighing device} \\ \text{(g)} \end{array} - \begin{array}{c} \text{Past weight on} \\ \text{weighing device} \\ \text{(g)} \end{array} \right| < 6 \text{ g}$$

wherein: "past weight" is the weight which was on the weighing device at the time when the expected ml. of pump flow was 4 ml. less that the present expected ml. of pump flow.

Additionally, during both collection and reinfusion, the computer will continually verify the functioning of the pumps by applying a function such as the above-set-forth function, and, if at any point, the magnitude of difference between current wt. and past wt. exceeds the allowable range, the device will shut down and the operator will be signaled to check for possible malfunctions (e.g. leaks in the system). Detecting an empty cell bag can be distinguished from a system malfunction based upon a predicted expected time occurance of the emptying.

During the reinfusion, the computer will count store the number of rotations undergone by blood pump 186a in its "reinfusion" direction. This number will be subsequently utilized in recalculating and adjusting the reinfusion pump (i.e. reverse direction) flow constant of the blood pump 186a, in accordance with the method of this invention.

At the end of reinfusion, the cell bag 237 will be completely empty as shown in FIG. 7f. At that point, the weighing device 235a will obtain the post-reinfusion weight in accordance with step 134 of the method (FIG. 3b).

Thereafter, the computer will calculate the a) weight of cell concentrate reinfused (step 136), b) weight of actual plasma collected (step 138), c) collection flow constants for the blood pump and cell pump (step 140), and d) a reinfusion flow constant for the blood pump (step 142). The desired number of cell pump rotations for the next collection cycle will be recalculated by the computer on the basis of the newly calculated flow constants and, the preset number of cell pump rotations will be accordingly reset for the next collection/reinfusion cycle.

The blood filter/bubble trap 240 of the device may consist of any type of outer housing or shell having positioned therein one or more materials operative to effect filtration of the blood and/or trapping of bubbles as the blood passes through the blood filter/bubble trap 240.

iii. A Preferred Blood Filter/Bubble Trap Usable in the Device of the Present Invention One presently preferred type of blood filter/bubble trap is shown separately in FIG. 8. This preferred blood filter/bubble trap 300 comprises an outer plastic shell 302 of generally cylindrical configuration. The shell is compressed to a flat, closed configuration at its top end 304 and bottom end 306. A filtration bag formed of a material approved for use in blood pathway and blood processing, (e.g. certain fabrics, filtration media or fine mesh materials, such as a nylon mesh) is positioned inside the shell 302. The opening size or mesh size of the mesh material or fabric or filtration material is preferably about 220 microns. Second 312 and third 314 inlet tubes pass through the closed bottom end 306 of the shell 302. A stand pipe 316 is fluidly connected to the third input tube 314 and extends upwardly therefrom with the confines of the shell 302.

In its preferred embodiment, the filter 300 is approximately 12 centimeters in length from the top edge 304 of the shell to the bottom edge 306. The stand pipe 316 is approximately 2 centimeters in length.

In normal operation, the preferred blood filter/bubble trap device shown in FIG. 8 is mounted in the device of the present invention (FIG. 7) such that the cell concentrate line 220 is connected to the first inlet tube 308, the reinfusion line 188 is connected to the second inlet tube 312 and the lower cell concentrate line is connected to the third inlet tube 314. When so mounted in the device of the present invention, the filter bag 310 will operate to strain or filter cell concentrate flowing into the blood filter/bubble trap 300 from the blood separation device 212a. Additionally, the presence of the stand pipe 316 within the blood filter/bubble trap 300 will insure that a quantity of blood or cell concentrate pools in the bottom of the inner chamber of the blood filter/bubble trap 300 before such blood or cell concentrate begins to flow down the lower cell concentrate line 242. The opening of the second inlet tube 312 which is connected to the reinfusion line 188a is generally flush with the inner floor or bottom of the interior of the shell 302. Thus, the opening into the second inlet tube 312 will routinely be maintained below an approximate 2 centimeter head of blood or cell concentrate. By this arrangement, cell concentrate flowing through the filter bag 310 will fall into the bottom of the chamber and will rise to the level of the top of the stand pipe 316 before flowing down the lower cell concentrate line 242. This will help to prevent turbulent cell concentrate containing aberrant bubbles from entering the lower cell concentrate line 242. Such pooling of the cell concentrate in the lower 2 centimeters of the blood filter/bubble trap 240 will allow the cell concentrate an opportunity to degas before beginning to flow down the lower cell concentrate line 242. Such will help to prevent the introduction of air or bubbles into the cell bag 237.

The foregoing detailed description has discussed only several illustrative embodiments or examples of the present invention. Those skilled in the art will recognize that numerous other embodiments, or additions, modifications, deletions and variations of the described embodiment, may be made without eliminating the novel and unobvious features and advantages of the present invention. It is intended that all such other embodiments, modifications, deletions and variations be included within the scope of the following claims.

What is claimed is:

1. An apheresis method comprising the steps of:
   (a) fluidly connecting a blood separation device to the vasculature of a human subject;
   (b) operating at least one pump to withdraw whole blood from the human subject and to move said whole blood into said separation device;
   (c) providing a single weighing device having a first blood fraction container and a second blood fraction container positioned thereon, such that said weighing device will measure the combined weight of the said first blood fraction container and said second blood fraction container, along with any material contained therein;
   (d) recording an initial weight on said weighing device when said first blood fraction container and said second blood fraction container are empty;
   (e) operating said separation device to fraction the whole blood into at least a first blood fraction and a second blood fraction;
   (f) recording a second weight on said weighing device after said first blood fraction and said second blood fraction have been collected in said first blood fraction container and said second blood fraction container;
   (g) providing a fluid connection between said first blood fraction container and said human subject;
   (h) operating at least one pump to reinfuse said first blood fraction, through said fluid connection, into said human subject; and
   (i) recording a third weight on said weighing device after said first blood fraction has been removed from said first blood fraction container reinfused into said human subject.

2. The method of claim 1 further comprising the step of:
   utilizing the weights recorded in steps (d) and (f) to calculate a new "collection" flow constant for said at least one pump based on the actual weight of blood pumped from the human subject into the separation device; and
   utilizing the new collection flow constant to adjust the calibration of said at least one pump.

3. The method of claim 1 further comprising the steps of:
   utilizing the weights recorded by the single weighing device to determine the actual weight of first blood fraction pumped by said at least one pump during reinfusion step (h); utilizing the actual weight of first blood fraction pumped during reinfusion to calculate a new reinfusion flow constant for the at least one pump; and, thereafter;
   adjusting the calibration of said at least one pump on the basis of the new reinfusion flow constant calculated therefore.

4. The method of claim 1 further comprising the step of:
   continually monitoring the change in weight on the weighing device as said first blood fraction is being reinfused into said human subject; and
   periodically comparing the change of weight on said weighing device to an expected change in weight calculated on the basis of the expected throughput of said at least one pump utilized for reinfusing said first blood faction; and
   determining whether the change in weight on said weighing device differs from the expected change in weight by more than a predetermined allowable amount and, if such differing is greater than said allowable amount, stopping said at least one pump, thereby stopping the reinfusion of said first blood fraction at that point.

5. The method of claim 1 wherein said first blood fraction comprises cell concentrate and said second blood fraction comprises plasma.

6. The method of claim 1 wherein the step (b) of operating at least one pump further comprises:
  operating one blood pump for pumping blood from the human donor into the separation device; and
  operating a separate first blood fraction collection pump for pumping said first blood fraction out of the separation device and into the first blood fraction container.

7. The method of claim 6 wherein the step of operating the first blood fraction collection pump further comprises initially setting the first blood fraction pump to pump a desired volume of first blood fraction into said first blood fraction containing such initial setting of the cell pump being based on an "initial" pump flow constant.

8. The method of claim 7 wherein the "initial" pump flow constant is a coarse setting selected by the operator based on an estimated pump throughout.

9. The method of claim 6 wherein the "initial" pump flow constant is an empirically determined value.

10. The method of claim 6 further comprising the steps of:
  utilizing the weights recorded by the single weighing device to determine the actual weight of first blood fraction pumped from the separation device into the first blood fraction container by the first blood fraction collection pump;
  utilizing the actual weight of first blood fraction pumped by said first blood fraction collection pump to calculate a new collection flow constant for said first blood fraction pump; and, thereafter,
  adjusting the calibration of the first blood fraction pump in accordance with the new collection flow constant calculated therefore.

11. The method of claim 6 further comprising the steps of:
  utilizing the weights recorded by the single weighing device to determine the actual weight of whole blood pumped by said blood pump from said human subject into said separation device;
  utilizing the actual weight of whole blood pumped by said blood pump to calculate a new collection flow constant for said blood pump; and, thereafter,
  adjusting the calibration of said blood pump in accordance with the new collection flow constant calculated therefore.

12. The method of claim 6 further comprising the steps of:
  operating a reinfusion pump for reinfusing the first blood fraction from said first blood fraction container into said human subject;
  utilizing the weights recorded by the single weighing device to determine the actual weight of first blood fraction pumped by said reinfusion pump from said first blood fraction container into said human subject;
  utilizing the actual weight of first blood fraction pumped by said reinfusion pump to calculate a new reinfusion flow constant for said reinfusion pump; and, thereafter,
  adjusting the calibration of said reinfusion pump in accordance with the new reinfusion flow constant calculated therefore.

13. The method of claim 12 wherein the steps of "operating one blood pump" and "operating a reinfusion pump" further comprise:
  positioning a single collection/reinfusion pump relative to the fluid connection between the human subject and the fluid connection between the first blood fraction container and the human subject such that said single collection/reinfusion pump may be alternately operated in a "collection" mode whereby whole blood is pumped from the human subject into the blood separation device and a "reinfusion" mode whereby the first blood fraction is pumped from the first blood fraction container into the human subject.
  operating the single collection/reinfusion pump to initially effect "collection" mode pumping of whole blood from the human subject into the blood separation device and to subsequently, effect "reinfusion" mode pumping of the first blood fraction from the first blood fraction container into the human subject.

14. The method of claim 1 wherein "providing a single weighing device having a first blood fraction container and a second blood fraction container positioned thereon further comprises:
  providing a single weighing device having positioned thereon a flexible plastic bag for collecting the first blood fraction and a separate container for collecting the second blood fraction.

* * * * *